(12) United States Patent
Perrett

(10) Patent No.: US 11,357,750 B2
(45) Date of Patent: Jun. 14, 2022

(54) CYSTEAMINE PRODRUGS

(71) Applicant: Children's Hospital Medical Center, Cincinnati, MA (US)

(72) Inventor: Stephen Perrett, Lawrenceville, NJ (US)

(73) Assignee: Children's Hospital Medical Center, Cincinnati, OH (US)

( * ) Notice: Subject to any disclaimer, the term of this patent is extended or adjusted under 35 U.S.C. 154(b) by 18 days.

(21) Appl. No.: 16/480,773

(22) PCT Filed: Jan. 25, 2018

(86) PCT No.: PCT/US2018/015218
§ 371 (c)(1),
(2) Date: Jul. 25, 2019

(87) PCT Pub. No.: WO2018/140594
PCT Pub. Date: Aug. 2, 2018

(65) Prior Publication Data
US 2020/0000762 A1    Jan. 2, 2020

Related U.S. Application Data

(60) Provisional application No. 62/466,589, filed on Mar. 3, 2017, provisional application No. 62/450,431, filed on Jan. 25, 2017.

(51) Int. Cl.
*A61K 31/25* (2006.01)
*C07C 323/60* (2006.01)
*A61K 31/573* (2006.01)

(52) U.S. Cl.
CPC ............ *A61K 31/25* (2013.01); *A61K 31/573* (2013.01); *C07C 323/60* (2013.01)

(58) Field of Classification Search
CPC ..... A61K 31/25; A61K 31/573; C07C 323/60
USPC ......................................................... 514/181
See application file for complete search history.

(56) References Cited

U.S. PATENT DOCUMENTS

| | | |
|---|---|---|
| 6,340,746 B1 | 1/2002 | Roberts et al. |
| 2009/0048154 A1 | 2/2009 | Chan et al. |
| 2014/0322315 A1 | 10/2014 | Dohil et al. |
| 2016/0102052 A1 | 4/2016 | O'neil et al. |
| 2017/0081279 A1 | 3/2017 | Nguyen |

FOREIGN PATENT DOCUMENTS

| | | |
|---|---|---|
| JP | 2006-503852 A | 2/2006 |
| JP | 2010-513366 A | 4/2010 |
| WO | WO 2018/140594 A1 | 8/2018 |

OTHER PUBLICATIONS

Extended European Search Report for European Patent Application No. 18745367.5, dated Oct. 13, 2020, 8 pages.
Frost, et al., "Synthesis of diacylated γ-glutamyl-cysteamine prodrugs, and in vitro evaluation of their cytotoxicity and intracellular delivery of cysteamine." European Journal of Medicinal Chemistry (Feb. 15, 2016); 109: 206-215.
Roberts, et al., "Thiazolidine Prodrugs of Cysteamine and Cysteine as Radioprotective Agents." Radiation Research (Aug. 1995); 143(2): 203-213.
International Preliminary Report on Patentability for International Application No. PCT/US2018/015218, dated Jul. 30, 2019, 6 pages.
International Search Report and Written Opinion for International Application No. PCT/US2018/015218, dated Apr. 13, 2018, 8 pages.

*Primary Examiner* — Kristin A Vajda
(74) *Attorney, Agent, or Firm* — McDermott Will & Emery LLP

(57) ABSTRACT

Described herein are prodrugs of cysteamine and pharmaceutically acceptable salts, solvates, and esters thereof. Also described herein are pharmaceutical compositions comprising prodrugs of cysteamine, or pharmaceutically acceptable salts, solvates, and esters thereof, and methods of treatment comprising administering prodrugs of cysteamine, or pharmaceutically acceptable salts, solvates, and esters thereof.

20 Claims, 16 Drawing Sheets

CYSTEAMINE PRODRUGS

CROSS-REFERENCE TO RELATED APPLICATIONS

This application is the U.S. National Stage application of International Patent Application No. PCT/US2018/015218, filed Jan. 25, 2018, which claims the benefit of priority of U.S. Provisional Application No. 62/450,431, filed Jan. 25, 2017, and U.S. Provisional Application No. 62/466,589, filed on Mar. 3, 2017, the entire contents of each of which are hereby incorporated by reference in its entirety.

BACKGROUND

Cystinosis is a rare, autosomal recessive disease caused by abnormal intra-lysosomal accumulation of the amino acid cystine within various tissues, including the spleen, liver, lymph nodes, kidney, bone marrow, eyes, and brain. Cysteamine is the only approved treatment for cystinosis. When taken regularly, cysteamine can deplete intracellular cystine by up to 90% (as measured in circulating white blood cells), and this has been shown to reduce the rate of progression to kidney failure/transplantation and also to obviate the need for thyroid replacement therapy. About 1000 children require lifelong treatment to prolong their lives and prevent deterioration of kidney function.

There are several problems associated with cysteamine which leads to low patient compliance. One of the major drawbacks of cysteamine is its short half-life—cysteamine is only active for about 5-6 hours, necessitating administration 4 times a day (i.e., every 6 hours). Cysteamine also has poor organoleptic properties and an unpleasant smell, which reduces patient compliance, particularly among children. Even as a bitartrate salt, cysteamine has an intensely unpleasant taste and smell, resulting in nausea and vomiting, and frequently causes disturbance of the gastrointestinal mucosa. Gastric or duodenal ulceration is a common side effect. Extensive first pass metabolism of cysteamine after oral administration leads to urinary excretion of its conjugates, an estimated bioavailability of 10-30%, and significant amounts of dimethyl sulfide and methane thiol exhaled in the breath and through the pores of the skin as body odor. Cysteamine must be administered in high doses, and requires the use of large solid dosages in the form of tablets and capsules. For example, 60-90 mg/kg/day of cysteamine is required to maintain a therapeutic plasma concentration; to achieve such a plasma concentration, subjects must ingest upwards of 1 g per dose about four times per day of the immediate release formulation (CYSTAGON®).

Conventionally, cysteamine is formulated as a bitartrate salt in an immediate release capsule (CYSTAGON®) and as a delayed release form (PROSCYBI®). Because of the drug's short half-life, CYSTAGON® must be administered every 6 hours, including at nighttime. The 6 hour intake of CYSTAGON®, despite disruption to sleep, is important because cystine levels significantly increase when administered at 9 hourly dosing, when compared to a 6 hour dosing interval. The delayed-release PROSCYBI® prolongs the period between dosing to 12 hour intervals. This dosage form alleviates the issue of sleep disturbance, but has problems of first pass metabolism resulting in low bioavailability, the release of strong smelling metabolites, and the gastric disturbance issues are not significantly addressed. The present disclosure provides for prodrugs of cysteamine which overcome the limitations of previous cysteamine formulations.

SUMMARY

In various embodiments, the present disclosure provides for compounds (i.e., prodrugs of cysteamine) according to formula (I),

and pharmaceutically acceptable salts, solvates, and esters thereof.

In certain embodiments, the X group of the compounds according to formula (I) is a pharmaceutically acceptable moiety, and R comprises a moiety which releases cysteamine after administration to a subject. In some embodiments, the number of R groups on X (i.e., n) can be any integer, for example a number from 1 to 100.

In some embodiments, X is selected from the group consisting of alkyl, alkenyl, alkynyl, carbocyclyl, and heterocyclyl. In particular embodiments, X is alkyl.

In other embodiments, $X(R)_n$ is derived from a carbohydrate, a sugar alcohol, or polymeric alcohol, wherein at least one —OH group of the carbohydrate, the sugar alcohol, or the polymeric alcohol is replaced by R. In still other embodiments, the carbohydrate is selected from the group consisting of a monosaccharide, a disaccharide, an oligosaccharide, a polysaccharide, cellulose, a modified cellulosic, and starch. In particular embodiments, $X(R)_n$ is derived from glycerol.

In some embodiments, R comprises cysteamine, or a substituted form thereof, which is linked to X through a linking group which can be cleaved in vivo, thereby releasing cysteamine. In further embodiments, the linking group forms a thiocarbonate or thioester which is hydrolyzed enzymatically in vivo, thereby releasing cysteamine.

In some embodiments, the compound of formula (I) has a structure according to formula (IIA), (IIB), or (IIE)

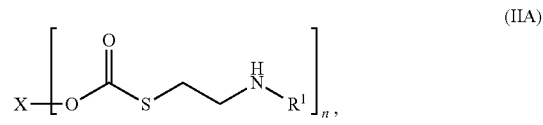

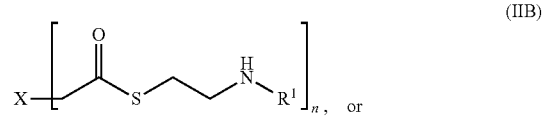

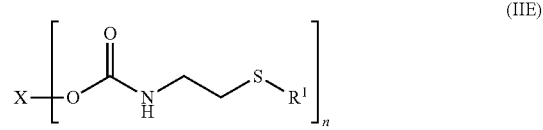

or a pharmaceutically acceptable salt, solvate, or ester thereof.

In particular embodiments, the compound of formula (I) has a structure according to formula (IIA).

In some embodiments, each $R^1$ is independently H or

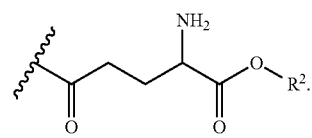

In some embodiments, each $R^2$ is independently H or an alkyl.

In some embodiments, the linking group forms a sulfoxide which is reduced and cleaved enzymatically in vivo, thereby releasing cysteamine. In some embodiments, the compound of formula (I) has structure according to formula (IIC)

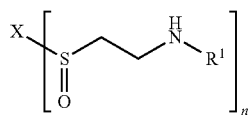

(IIC)

or a pharmaceutically acceptable salt, solvate, or ester thereof,

In some embodiments, each $R^1$ is independently H or

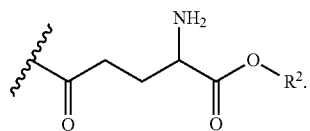

In some embodiments, each $R^2$ is independently H or an alkyl.

In some embodiments, the linking group forms a disulfide bond which is reduced in vivo, thereby releasing cysteamine. In some embodiments, the compounds of formula (I) have a structure according to formula (IID)

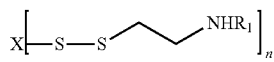

(IIID)

or a pharmaceutically acceptable salt, solvate, or ester thereof.

In some embodiments, each $R^1$ is independently H or

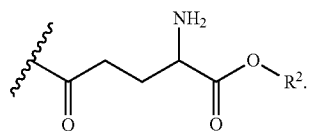

In some embodiments, each $R^2$ is independently H or an alkyl.

In some embodiments, the compounds of formula (I) have a structure according to formula (III)

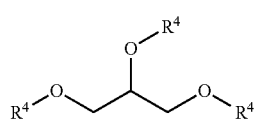

(III)

In some embodiments, each $R^4$ is independently H,

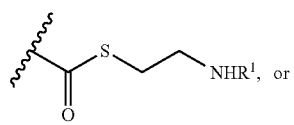

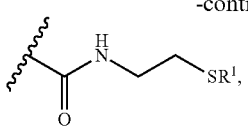

and at least one $R^4$ is

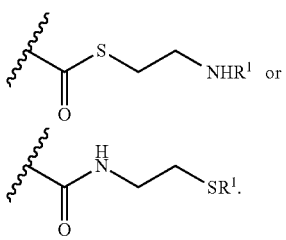

In particular embodiments, each $R^4$ is independently H

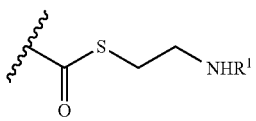

and at least one $R^4$ is

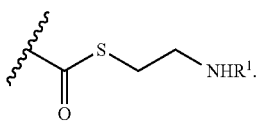

In some embodiments, each $R^1$ is independently H or

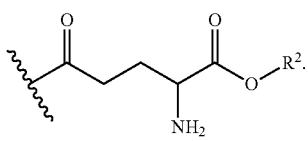

In some embodiments, each $R^2$ is independently H or alkyl.

In other embodiments, the present disclosure provides for pharmaceutical compositions comprising at least one compound according to formula (I), (IIA), (IIB), (IIC), (IID), (IIE), and (III), and pharmaceutically acceptable salts, solvates, or esters thereof. In some embodiments, the pharmaceutical composition further comprises a corticosteroid.

In still other embodiments, the disclosure provides methods of treating a disease a subject in need thereof, comprising administering at least one compound of formula (I), (IIA), (IIB), (IIC), (IID), (IIE), and (III), and pharmaceutically acceptable salts, solvates, or esters thereof. In some embodiments, the method further comprises administering a corticosteroid. In some embodiments, the disease is cystinosis, cystinuria, non-alcoholic fatty liver disease, non-alcoholic steatohepatitis, Huntington's disease, Parkinson's disease, Rett Syndrome, Parkinson's disease, malaria, neuropsychiatric disorders, cancer, cystic fibrosis, depressive disorder, inherited mitochondrial disease (e.g., Leigh syndrome), HIV, schizophrenia, infantile neuronal ceroid lipofuscinosis, Crohn disease, ulcerative colitis, asthma, or Waldenstrom's macroglobulinemia. In some embodiments, the cancer is lymphoma or myeloma.

BRIEF DESCRIPTION OF THE FIGURES

The skilled artisan will understand that the drawings are primarily for illustrative purposes and are not intended to limit the scope of the inventive subject matter described herein.

DETAILED DESCRIPTION

Definitions

Figure 1A:
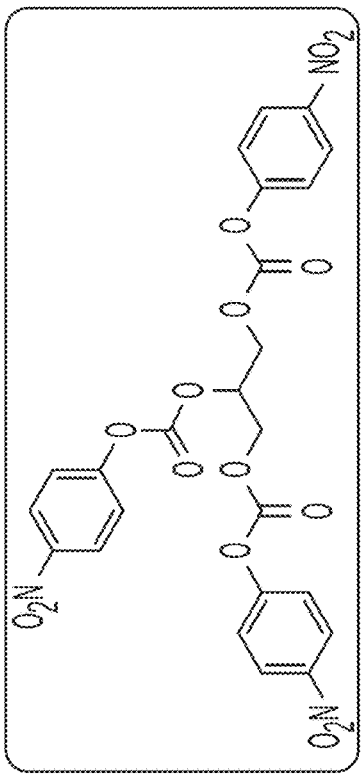
FIG. 1A is a chromatogram illustrating the purity profile for Int-1 after recrystallization.
Figure 1A:
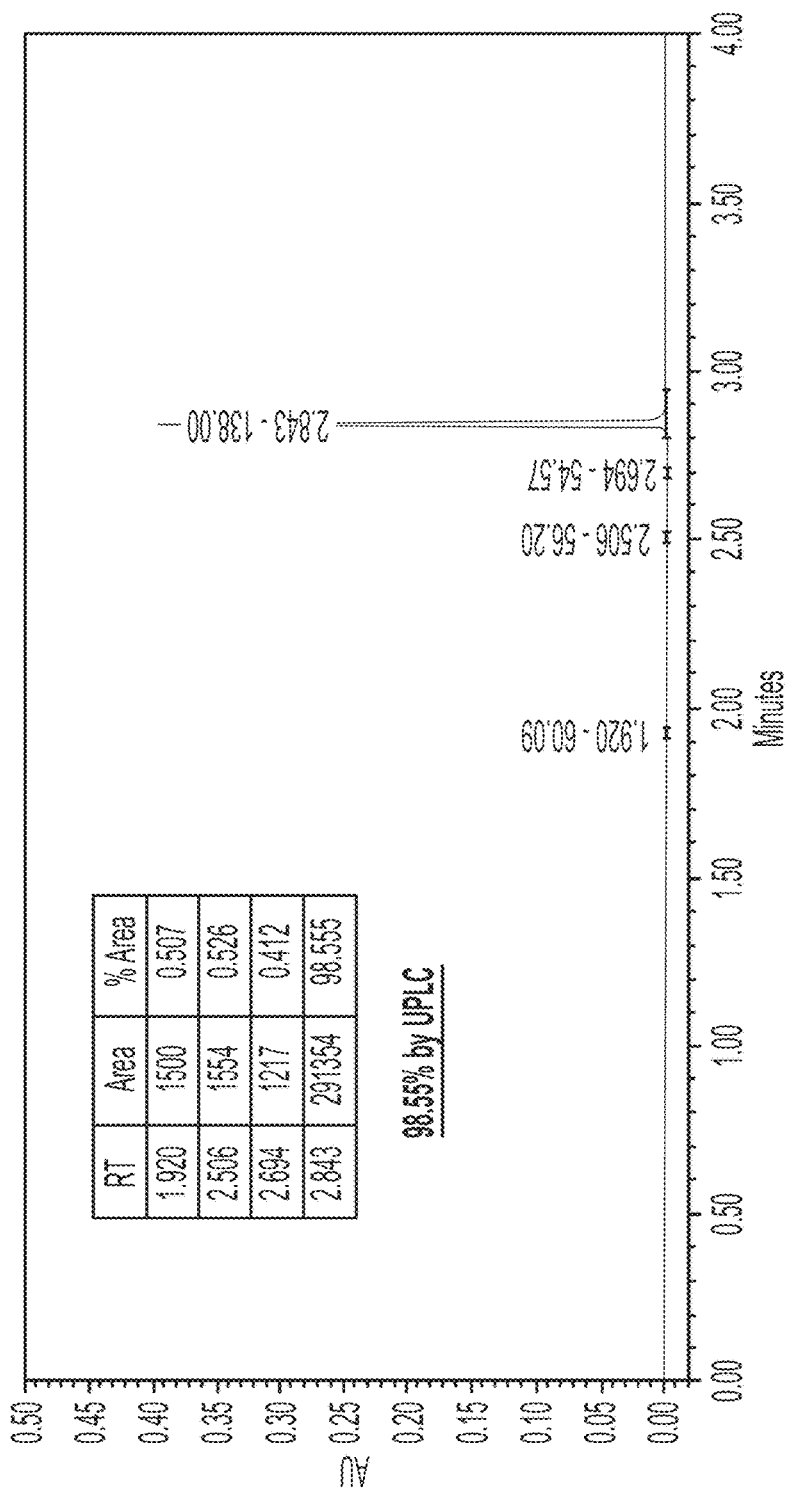

While the following terms are believed to be well understood by one of ordinary skill in the art, the following definitions are set forth to facilitate explanation of the presently disclosed subject matter.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity. As such, the terms "a" (or "an"), "one or more" and "at least one" are used interchangeably herein.

The verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "pharmaceutically acceptable solvates" refers to a complex of variable stoichiometry formed by a solute and solvent. Such solvents for the purpose of the application may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "pharmaceutically acceptable esters" include those obtained by replacing a hydrogen on an acidic group with an alkyl group, for example by reacting the acid group with an alcohol or a haloalkyl group. Examples of esters include, but are not limited to, replacing the hydrogen on an —C(O)OH group with an alkyl to form an —C(O)Oalkyl.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of cysteamine according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

"Aliphatic" or "aliphatic group" refers to hydrocarbons (i.e. compounds composed of carbon and hydrogen) which are non-aromatic compounds. Aliphatics include alkyl, alkenyl, alkynyl, cycloalkyl, cycloalkenyl, cycloalkynyl and non-aromatic heterocyclyl, each optionally substituted as defined herein.

"Aromatic" or "aromatic group" refers to a planar, unsaturated ring of atoms that is stabilized by an interaction of the bonds forming the ring. Aromatics include aryl and heteroaryl, each optionally substituted as defined herein.

"Alkyl" or "alkyl group" refers to a fully saturated, straight or branched hydrocarbon chain having from one to twelve carbon atoms, wherein at least one bond to hydrogen is replaced by a bond to an —R group. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, the alkyl is optionally substituted as defined herein.

"Alkenyl" or "alkenyl group" refers to a straight or branched hydrocarbon chain having from two to twelve carbon atoms, having one or more carbon-carbon double bonds, wherein at least one bond to hydrogen is replaced by a bond to an —R group. Alkenyl groups comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4 octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkenyl group is optionally substituted as defined herein, and may also be optionally substituted as defined herein.

"Alkynyl" or "alkynyl group" refers to a straight or branched hydrocarbon chain having from two to twelve carbon atoms, and having one or more carbon-carbon triple bonds, wherein at least one bond to hydrogen is replaced by a bond to an —R group. Alkynyl groups comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkynyl group is optionally substituted as defined herein.

"Aryl" or "aryl group" refers to a hydrocarbon ring system comprising hydrogen, 6 to 18 carbon atoms and at least one aromatic ring, wherein at least one bond to hydrogen is replaced by a bond to an —R group. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene, each of which is substituted with least one hydroxyl group. Unless stated otherwise specifically in the specification, "aryl group" is optionally substituted as defined herein.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group is optionally substituted as defined herein.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, wherein at least one bond to hydrogen is replaced by a bond to an —R group. Monocyclic cycloalkyls include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted as defined herein.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, wherein at least one bond to hydrogen is replaced by a bond to an —R group. Monocyclic cycloalkenyls include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group may be optionally substituted as defined herein.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms. Monocyclic cycloalkynyl includes, for example, cycloheptynyl, cyclooctynyl, and the like. Unless otherwise stated specifically in the specification, a cycloalkynyl group is optionally substituted as defined herein.

"Heterocyclyl," "heterocyclic ring" or "heterocycle" refers to a stable 3- to 20-membered ring which consists of two to twelve carbon atoms and from one to six heteroatoms selected from the group consisting of nitrogen, oxygen and sulfur, wherein at least one bond to hydrogen is replaced by a bond to an —R group. Heterocyclycl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the hydroxyheterocyclyl can be optionally oxidized; the nitrogen atom can be optionally quaternized; and the hydroxyheterocyclyl can be partially or fully saturated. Examples of such heterocyclyl include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group is optionally substituted as defined herein.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group is optionally substituted as defined herein.

The term "polymeric alcohol" refers to compounds containing multiple hydroxyl groups, including compounds having the formula —[CH$_2$CH(OH)]$_q$, wherein q is a number from 2 to 100, and optionally wherein at least one hydrogen atom is replaced by a bond to a hydroxyl group. Examples include, but are not limited to, polyvinyl alcohol. Unless stated otherwise specifically in the specification, a polymeric is optionally substituted as defined herein.

The term "substituted" used herein means any of the above groups (i.e., alkyl, alkenyl, alkynyl, aryl, carbocyclyl, cycloalkyl, cycloalkenyl, cycloalkynyl, heterocyclyl, or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O) NR$_g$R$_h$, —NR$_g$C(=O)OR$_h$, —NR$_g$SO$_2$R$_h$, —OC(=O) NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O) OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

"Thiocarbonate" or "thiocarbonate group" refers to a divalent radical having the following structure:

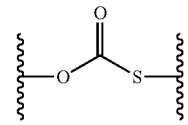

"Thioester" or "thioester group" refers to a divalent radical having the following structure:

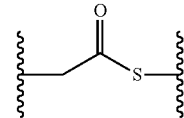

"Disulfide" or "disulfide group" refers to a divalent radical having the following structure:

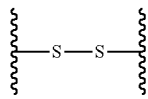

"Sulfoxide" or "sulfoxide group" refers to a divalent radical having the following structure:

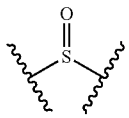

As used herein, "aminocarbonate" refers to a divalent radical having the following structure:

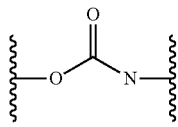 [SMILES: *NC(=O)O*]

As used herein, "thio" refers to a —SH radical.
As used herein, "hydroxyl" refers to a —OH radical.

Cysteamine Prodrugs

Cysteamine is a therapeutic agent having the following structure:

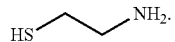

Cysteamine is also known as 2-aminoethane-1-thiol.

Disclosed herein are prodrugs of cysteamine. In embodiments, the prodrugs have a structure according to formula (I),

or pharmaceutically acceptable salts, solvates, or esters thereof,
wherein:
X is a pharmaceutically acceptable moiety;
R comprises a moiety which releases cysteamine after administration to a subject; and
n is a number from 1 to 100.

X can be any pharmaceutically acceptable moiety. In this context, "pharmaceutically acceptable moiety" means that after administration and release of cysteamine from the R moiety or moieties, metabolites comprising the X moiety are clinically acceptable in the amounts produced in vivo. For example, glycerol, which has 3 hydroxyl groups, can be converted to a mono-, di-, or tris-carbonate, which is then reacted with cysteamine to form a glycerylthiocarbonate of cysteamine. The resulting glycerylthiocarbonate of cysteamine can optionally be further reacted to substitute the amine nitrogen of the cysteamine moiety. In such a reaction, the glyceryl hydrocarbon backbone is represented by X, and R is e.g., a —O—C(O)—S—(CH$_2$)$_2$—NHR$^1$ moiety (see e.g., formula (II)). Similarly, when the compounds of formula (I) are prepared from other hydroxyl-containing compound such as sugar alcohols, carbohydrates, starches, etc., X represents the, e.g., sugar alcohol, carbohydrate, or starch backbone, linked via a physiologically cleavable linking group (e.g., thiocarbonate, thioester, disulfide, sulfoxide, etc.) to a substituted or unsubstituted cysteamine moiety.

In some embodiments, X can be substituted with at least about 2 hydroxyl groups, e.g., at least about 3, at least about 4, at least about 5, at least about 6, at least about 7, at least about 8, at least about 9, at least about 10 hydroxyl groups, etc. In other embodiments, X can be substituted with about 2 to about 100 hydroxyl groups, e.g., about 5, about 10, about 15, about 20, about 25, about 30, about 35, about 40, about 45, about 50, about 55, about 60, about 65, about 70, about 75, about 80, about 85, about 90, or about 95 hydroxyl groups, including all values and subranges therebetween.

In some embodiments, n is a number from about 2 to about 100, e.g., about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, or about 95 hydroxyl groups, including all values and subranges therebetween. In certain embodiments, n is a number from about 2 to about 10.

In embodiments, cysteamine is linked to X through the thiol group of cysteamine by formation of a thiocarbonate to thereby mask the thiol group. Masking the thiol group significantly reduces or eliminates unpleasant smells which can be associated with the administration of cysteamine, as well significantly reduce the amount of the cysteamine lost through first past metabolism. In other embodiments, cysteamine is linked to X through the amino group of cysteamine by formation of an aminocarbonate.

In embodiments, X is selected from the group consisting of physiologically acceptable aliphatics, such as alkyls, alkenyls, alkynyls, carbocyclyls or heterocyclyls.

In other embodiments, X is selected from the group consisting of physiologically acceptable aromatics, such as aryls or heteroaryls.

Compounds of formula (I) can be prepared by the appropriate substitution of one or more —OH groups on a precursor (e.g., X(OH)$_n$) to form one or more corresponding —R groups on X. Non-limiting examples of suitable compounds of formula X(OH)$_n$ include glycerol, thioglycerol, ethylene glycol, polyethylene glycol, polyvinylalcohol, and the like. Other examples of X(OH)$_n$ include carbohydrates, sugar alcohols, polymeric alcohols, and the like. Still other examples of X(OH)$_n$ include polysaccharides such as cellulose or starch, or modified forms thereof (e.g., esters and/or ethers thereof).

Non-limiting examples of sugar alcohols include mannitol, sorbitol, xylitol, maltitol, arabitol, ribitol, dulcitol, iditol, isomalt, lactitol, erythritol, and the like. Non-limiting examples of carbohydrates include monosaccharides, disaccharides, oligosaccharides, polysaccharides, celluloses, modified cellulosics, starches, and the like. Further examples of carbohydrates include 5- and 6-membered ring monosaccharides such as ribose, furanose, and mannose, disaccharides such lactose, sucrose, maltose, agrose, polysaccharides and oligosaccharides such as dextrins and maltodextrins, and modified cellulosics such as microcrystalline cellulose, silicified microcrystalline cellulose, mannitol-microcrystalline cellulose, hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethylcellulose and other cellulose derivatives.

In some embodiments, —R comprises a moiety which releases cysteamine after administration to a subject, for example cysteamine (or substituted forms thereof) linked to X through a linking group which can be cleaved in-vivo, thereby releasing cysteamine. Non-limiting examples of moieties which can release cysteamine after administration to a subject include moieties having a linking group which is acid labile, an enzymatically cleavable linking group, a hydrolysable linking group, a disulfide which is cleaved by glutathione and enzymes, and other linking groups which can be cleaved by intracellular or extracellular enzymes. In particular embodiments, —R comprises cysteamine and a linking group wherein, after administration to a subject, enzymes cleave the linking group to release cysteamine.

In some embodiments, R is selected from the group consisting of:

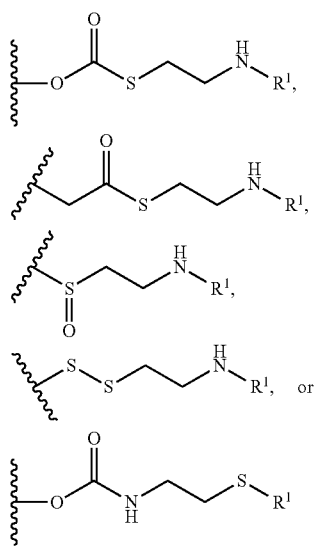

wherein $R^1$ is defined herein.

Although the above —R groups show linkage of cysteamine (or a derivative thereof) to X through the sulfur atom of cysteamine, the present disclose is not limited to such. Linkage of cysteamine (or a derivative thereof) may also occur through the nitrogen atom of cysteamine (depending on the synthetic route, the use of protecting groups, etc.). For example, in some embodiments, the percent of cysteamine moieties linked to X through the sulfur atom of cysteamine is in the range of from about 0% to about 100%, e.g., about 9%, about 5%, about 10%, about 15%, about 20%0, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, inclusive of all values and subranges therein. In other embodiments, the percent of cysteamine moieties linked to X through the nitrogen atom of cysteamine is in the range of from about 0% to about 100%, e.g., about 9%, about 5%, about 10%, about 15%, about 20%, about 25%, about 30%, about 35%, about 40%, about 45%, about 50%, about 55%, about 600, about 65%, about 70%, about 75%, about 80%, about 85%, about 900%, about 95%, about 96%, about 97%, about 98%, about 99%, or about 100%, inclusive of all values and subranges therein. Thus, in certain embodiments, a portion of the linkages of cysteamine (or a derivative thereof) to X may be through the sulfur atom of cysteamine, and a portion of the linkages to X may be through the nitrogen atom of cysteamine. In some such embodiments, the ratio of linkage through the sulfur atom to linkages through the nitrogen atom is in the range of from about 1:99 to about 99:1, including about 1:99, about 5:95, about 10:90, about 15:85, about 20:80, about 25:75, about 30:70, about 35:65, about 40:60, about 45:55, about 50:50, about 55:45, about 60:40, about 65:45, about 70:30, about 75, 25, about 80:80, about 85:15, about 90:10, about 95:5, and about 99:1, inclusive of all values and subranges therebetween.

In particular embodiments, R is a moiety which includes a thiocarbonate group and cysteamine or a substituted form thereof, e.g., —O—C(O)—S—$(CH_2)_2NHR_1$. In other particular embodiments, R is a moiety which includes a thioester group and cysteamine or a substituted form thereof, e.g., —$CH_2$—C(O)—S—$(CH_2)_2NHR_1$. In still other particular embodiments, R is a moiety which includes a aminocarbonate group and cysteamine or a substituted form thereof, e.g., —O—C(O)—NH—$(CH_2)_2SR_1$. Pancreatic lipase can hydrolyze thiocarbonates, thioesters, and aminocarbonates to produce corresponding carboxylic acids and thiols. Pancreatic lipase, also known as pancreatic triacylglycerol lipase, is an enzyme secreted from the pancreas which hydrolyzes fat molecules, such as triglycerides to yield corresponding monoglycerides and fatty acids. Without being bound by theory, after the prodrugs exit the stomach, pancreatic lipase hydrolyzes the thiocarbonate group, thioester group, or aminocarbonate group of the prodrugs disclosed herein to release cysteamine in the lower gastrointestinal tract (e.g., in the duodenum). In some embodiments, metabolism of the prodrugs described herein by pancreatic lipases may provide for the sustained release of cysteamine which may reduce the frequency of dosing. In other embodiments, the prodrugs described herein reduce first pass metabolism by preventing release of cysteamine until the cysteamine prodrug as described herein reaches the lower gastrointestinal tract. In still other embodiments, the delay in cysteamine release may reduce gastric irritation and the bad-smell associated with cysteamine.

In some embodiments, the cysteamine prodrugs disclosed herein have a structure according to formula (IIA), (IIB), or (IIE):

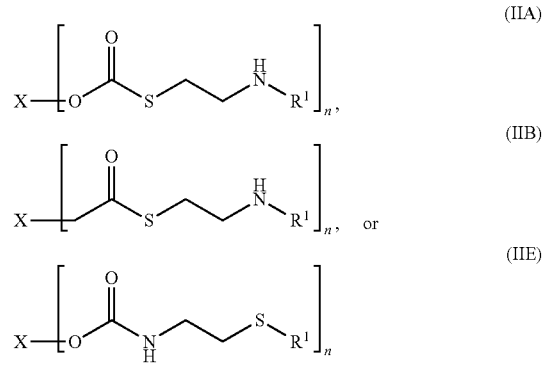

or a pharmaceutically acceptable salt, solvate, or ester thereof.

In other embodiments, R is a moiety which includes a sulfoxide group and cysteamine or a substituted form thereof, e.g., —S(O)—$(CH_2)_2NHR_1$. Without being bound by theory, sulfoxide reductases can reduce the sulfoxides to the corresponding thioester, and carbon-sulfur lyases can liberate cysteamine or a substituted form thereof in vivo. Thus, in some embodiments, the cysteamine prodrugs disclosed herein have a structure according to formula (IIC)

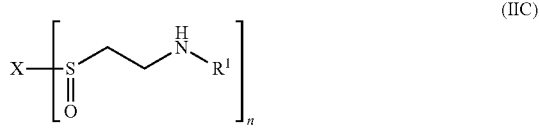

(IIC)

or a pharmaceutically acceptable salt, solvate, or ester thereof.

In still other embodiments, R is a moiety which includes a disulfide bond and cysteamine or a substituted form thereof, e.g., —S—S—(CH$_2$)$_2$NHR$_1$. Without being bound by theory, a disulfide group can be reduced in vivo Fto liberate cysteamine or a substituted form thereof. Thus, in some embodiments, the cysteamine prodrugs disclosed herein have a structure according to formula (IID)

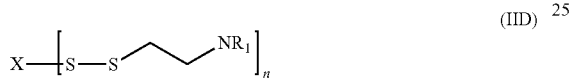

(IID)

In various embodiments, R$^1$ is an acyl group of the formula —C(O)—R$^3$, where R$^3$ can be an alkyl, alkenyl, alkynyl, or saturated or unsaturated cycloalkyl group, each of which are optionally substituted with one or more substituents such as hydroxyl, amino, carboxyl, thio, etc. In particular embodiments, R$^3$ is an amino acid residue such as a residue of aspartic acid, glutamic acid, etc. wherein a carboxylic acid group of the amino acid is reacted with the amino group of the cysteamine moiety of formula (II) in which R$^1$ is H.

The prodrugs according to the present disclosure do not include compounds having the following structure:

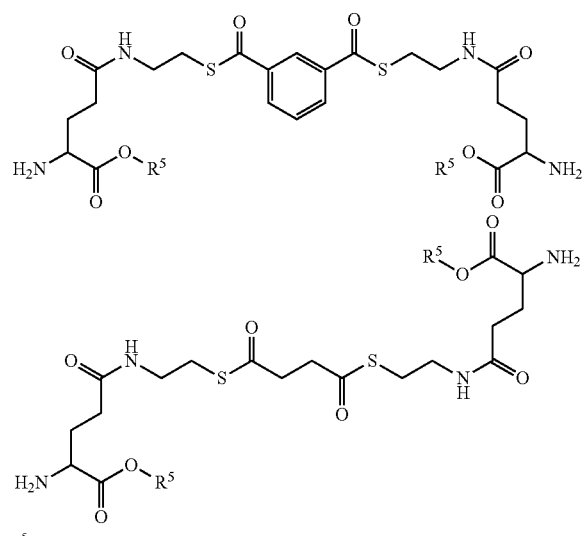

R$^5$ = CH$_2$CH$_3$, CH$_2$CH$_2$CH$_3$, or CH$_2$CH$_2$CH$_2$CH$_3$

In embodiments, X(R)$_n$ is prepared by the appropriate substitution of glycerol or an analog thereof. Glycerol is a low molecular weight, pharmaceutically acceptable moiety which can be derivatized to form the prodrugs described herein. A "glycerol analog" refers to glycerol with an elongated carbon chain and/or glycerol in which at least one oxygen atom is replacement by a different heteroatom, such as sulfur or nitrogen (provided that the glycerol analog can be reacted to form a group —R as described herein). In some embodiments, the glycerol backbone may also allow for the prodrug to be formulated as a liquid composition which allows for dose titration and may help improve patient compliance, e.g., by providing an easy-to-swallow liquid formulation.

Accordingly, in some embodiments, the glycerol prodrugs of cysteamine disclosed herein have a structure according to formula (III)

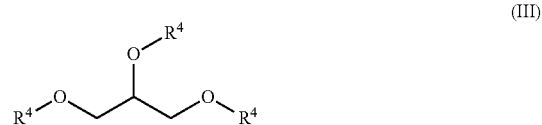

(III)

or a pharmaceutically acceptable solvate, or ester thereof, wherein:

each R$^4$ is independently H,

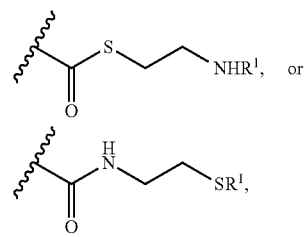

and at least one R$^4$ is

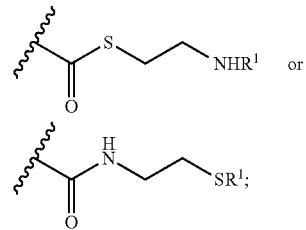

each R$^1$ is independently H or a physiologically acceptable and cleavable moiety
such as —C(O)—R$^3$ as described herein, including

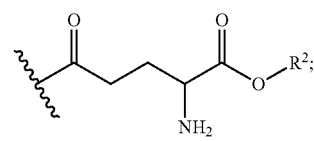

and each R$^2$ is independently H or alkyl.

In further embodiments, the prodrug according to formula (III) has one of the following structures:

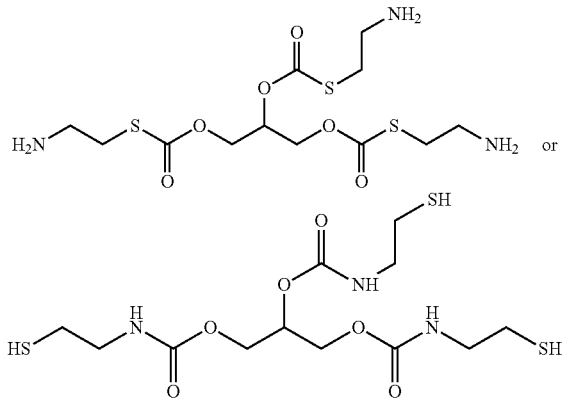

Although the above structure shows functionalization of all three hydroxyl groups of glycerol, in practice, the maximum theoretical functionalization of the hydroxyl groups of glycerol, or more broadly, the available functional groups of any precursor of $X(R)_n$ may not be achieved. For example, in some embodiments, the percent functionalization (i.e., actual/theoretical*100) of the total number of hydroxyl groups of a precursor of $X(R)_n$ such as glycerol (but also including any of the precursors of $X(R)_n$ disclosed herein) is in the range of from about 30% to about 100%, e.g., about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, inclusive of all values and subranges therein.

In embodiments, the thiol and/or amino terminus of cysteamine in the prodrugs of the present disclosure may be synthetically modified. In embodiments, gamma glutamic acid (or gamma glutamate) may be covalently bound to the amino terminus through the creation of an amide bond. Accordingly, in some embodiments, the prodrug comprises at least one R group having the following structure:

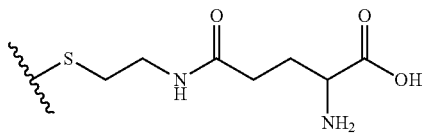

Gamma glutamyl transpeptidase (GGT) is a membrane-bound enzyme found on the surface of most cells, and is overexpressed by cystinotic cells. GGT is known to internalize gamma glutamyl amino acids. In some embodiments, covalently attaching gamma glutamyl to the cysteamine prodrugs described herein can improve cellular uptake. In other embodiments, this modification may also improve bioavailability by reducing first pass metabolism and excretion, which reduces the dosage amount and the side effects associated with cysteamine.

The terminal carboxylic acid moieties of the gamma glutamyl cysteamine prodrugs described herein may be synthetically modified to improve oral bioavailability. In embodiments, the carboxylic acid moieties can be esterified. The ester groups can be hydrolyzed after administration by an esterase.

Pharmaceutical Compositions and Formulations

In embodiments, the present disclosure provides for pharmaceutical compositions comprising cysteamine prodrugs or pharmaceutical salts, solvates, or esters thereof.

In one embodiment, a pharmaceutical composition comprises one or more compounds of formula (I), (IIA), (IIB), (IIC), (IID), (IIE), or (III), or pharmaceutically acceptable salts, solvates, or esters thereof. In some embodiments, one or more of the compounds of formula (I), (IIA), (IIB), (IIC), (IID), (IIE), or (III), or pharmaceutically acceptable salts, solvates, or esters thereof are administered to treat cystinosis and other metabolic and neurodegenerative diseases including or cystinuria, non-alcoholic fatty liver disease (NAFLD), non-alcoholic steatohepatitis (NASH), chronic kidney disease, Huntington's disease, Parkinson's disease, Rett Syndrome, Parkinson's disease, malaria, neuropsychiatric disorders, cancer (e.g., lymphoma, myeloma, etc.), cystic fibrosis, depressive disorder, inherited mitochondrial disease (e.g., Leigh syndrome), HIV, schizophrenia, infantile neuronal ceroid lipofuscinosis, Crohn disease, ulcerative colitis, and Waldenstrom's macroglobulinemia.

In one embodiment of the present disclosure, a pharmaceutical composition comprises a therapeutically effective amount of one or more compounds of formula (I), (IIA), (IIB), (IIC), (IID), (IIE), or (III), or pharmaceutically acceptable salts, solvates, or esters thereof.

In one embodiment, a pharmaceutical composition, as described herein, comprising one or more compounds of formula (I), (IIA), (IIB), (IIC), (IID), (IIE), or (III), or pharmaceutically acceptable salts, solvates, or esters thereof, further comprises one or more additional therapeutically active agents. In some embodiments, one or more additional therapeutically active agents include common allergy-related medications including, without limitations, antihistamines (i.e., terfenadine, astemazole, loratadine); decongestants (i.e., pseudoephedrine); steroids (i.e., beclomethasone, triamcinolone, budesonide, fluticasone); non-steroidal anti-inflammatory medications (i.e., cromolyn sodium, nedocromil); epinephrine; and bronchodilators (i.e., beta-agonists, anticholinergics). In a particular embodiment, one or more additional therapeutically active agents are corticosteroids. Corticosteroids compatible with the present disclosure include, but are not limited to, hydrocortisone, prednisone, prednisolone, methylprednisolone, dexamethasone, betamethasone, budesonide, fluticasone, flunisolide, ciclesonide, mometasone, beclomethasone, tixocortol and salts, solvates, and esters thereof.

In a further embodiment of the present disclosure, a pharmaceutical composition comprising one or more compounds of formula (I), (IIA), (IIB), (IIC), (IID), (IIE), or (III), or pharmaceutically acceptable salts, solvates, or esters thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (I), (IIA), (IIB), (IIC), (IID), (IIE), or (III), or pharmaceutically acceptable salts, solvates, or esters thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I), (II), (IIA), (IIB), (IIC), (IID), (IIE), or (III), or pharmaceutically acceptable salts, solvates, or esters thereof, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent.

The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. Suitable materials which may be used for an enteric coating include, but are not limited to, methyl acrylate-methacrylic acid copolymers, methyl methacrylate-methacrylic acid copolymers, cellulose acetate phthalate, cellulose acetate succinate, hydroxypropyl methyl cellulose phthalate, hydroxypropyl methyl cellulose acetate succinate, polyvinyl acetate phthalate, shellac, cellulose acetate trimellitate, sodium alginate, zein, and the like.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (I), (IIA), (IIB), (IIC), (IID), (IIE), or (III), and pharmaceutically acceptable salts, solvates, and esters thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Flavoring agents may also be used to improve the taste. Flavoring agents include artificial and natural (e.g., fruit extracts) agents such as mint, cherry, anise, peach, apricot, liquorice, raspberry, vanilla, and the like.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In other embodiments the compound of the present disclosure are administered by the intravenous route. In further embodiments, the parenteral administration may be provided in a bolus or by infusion.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In various aspects, the amount of the compound of formula (I), (IIA), (IIB), (IIC), (IID), (IIE), or (II), or a pharmaceutically acceptable salt, solvate, or ester thereof, can be administered at about 0.001 mg/kg to about 500 mg/kg body weight, e.g., about 0.01 mg/kg, about 0.1 mg/kg, about 1 mg/kg, about 10 mg/kg, about 100 mg/kg, about 200 mg/kg, about 300 mg/kg, about 400 mg/kg, including all values and subranges therebetween.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

Methods of Treatment

In embodiments, cysteamine prodrugs and pharmaceutically acceptable salts, solvates, or esters thereof of the present disclosure, may be used to treat cystinosis and other metabolic and neurodegenerative diseases including cystinuria, non-alcoholic fatty liver disease (NAFLD), non-alcoholic steatohepatitis (NASH) Huntington's disease, Parkinson's disease, Rett Syndrome, Parkinson's disease, malaria, neuropsychiatric disorders, cancer (e.g., lymphoma, myeloma, etc.), cystic fibrosis, depressive disorder, inherited mitochondrial disease (e.g., Leigh syndrome), HIV, schizophrenia, infantile neuronal ceroid lipofuscinosis, Crohn disease, ulcerative colitis, asthma, and Waldenstrom's macroglobulinemia.

In embodiments, cysteamine prodrugs and pharmaceutically acceptable salts, solvates, and esters thereof (e.g. the compounds of the present disclosure as discussed above), may be used as an intracellular antioxidant. Thiol containing compounds such as cysteamine are among the most important and active intracellular antioxidants.

In embodiments, cysteamine prodrugs and pharmaceutically acceptable salts, solvates, and esters thereof (e.g. the compounds of the present disclosure as discussed above), may be used as a radioprotectant. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have appeared demonstrating a protective effect of cysteamine against the hepatotoxic agents acetaminophen, bromobenzene, and phalloidine.

Synthetic Scheme

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Starting materials are either commercially available or made by known procedures in the reported literature or as illustrated. Compounds of the present disclosure can be synthesized by following the steps outlined in General Scheme A, B, C, D, and/or E. Those skilled in the art will of synthetic organic chemistry will appreciate that the selection of the precursor $X(OH)_n$ will partially depend on the desired product and/or the reagents used, e.g., as various mechanisms require a primary or secondary alcohol. As shown in General Scheme A below, a hydroxyl group of a precursor $X(OH)_n$ to $X(R)_n$ is first converted to a carbonate, e.g., using an anhydride which is activated by a suitable Lewis or Brønstedt acid or other catalyst, and then allowed to react with cysteamine (or cysteamine in which the amine group is protected with a protected group (PG)) to form the prodrugs of the present disclosure. Alternatively, as shown in General Scheme B, cysteamine (or the amino-protected derivative) can be converted a thiocarbonate, e.g., using an anhydride which is activated by suitable Lewis or Brønstedt acid or other catalyst, and then allowed to react with a hydroxyl group of X—OH to form the prodrugs of the present disclosure containing one or more thiocarbonate group. As shown in General Scheme C, the hydroxyl group of a precursor $X(OH)_n$ can be converted to a carboxylic acid directly or via an aldehyde, e.g., using an well-known oxidizing agents, and then allowed to react with cysteamine to form the thioester prodrugs of the present disclosure. As shown in General Scheme D, the hydroxyl group of a precursor $X(OH)_n$ can be converted to a halide, which is then reacted with cysteamine (or the amino-protected derivative) followed by oxidation of sulfur to form the sulfoxide prodrugs of the present disclosure. General Scheme E illustrates the formation of the disulfide containing prodrugs, which are prepared by converting the hydroxyl group of a precursor $X(OH)_n$ to a halide and then to a thiol, followed by the addition of cysteamine (or the amino-protected derivative) to form the disulfide prodrugs of the present disclosure. The formation of the disulfide prodrugs can be aided by the use of reagents known in the art which prevent unwanted dimerization of thiols, e.g., BtCl/BtH General Scheme A.

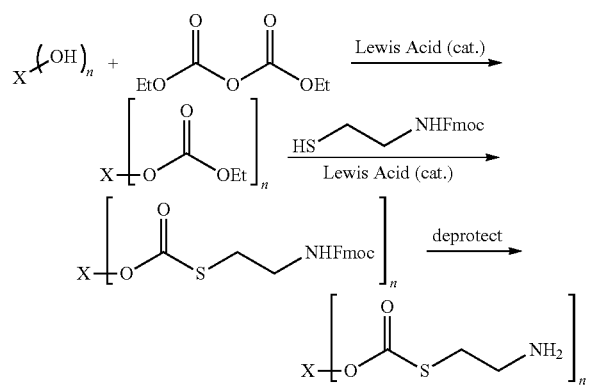

General Scheme B.

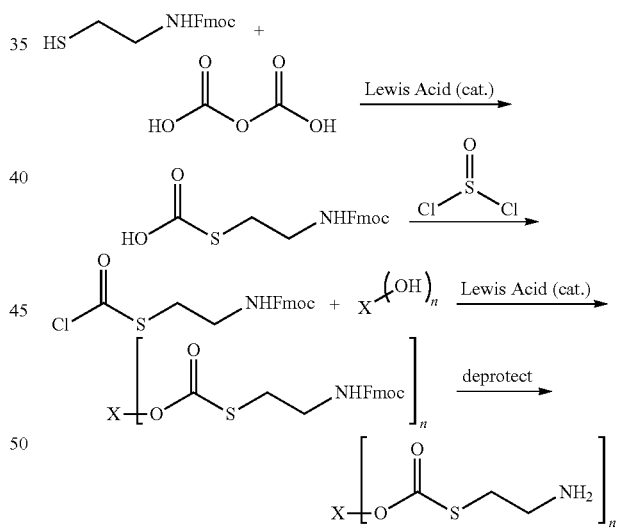

General Scheme C.

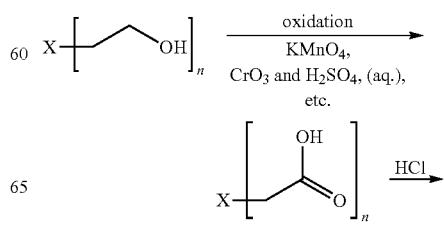

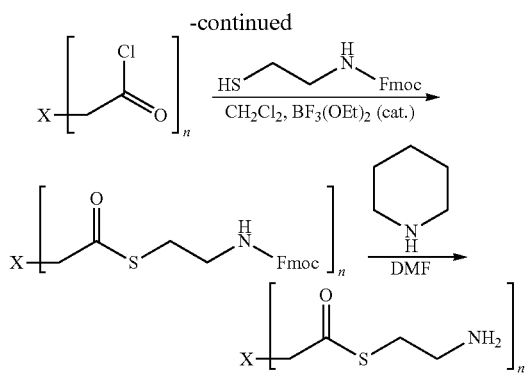

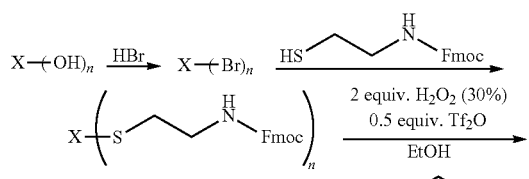

General Scheme D.

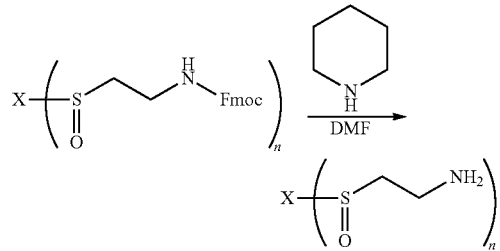

General Scheme E.

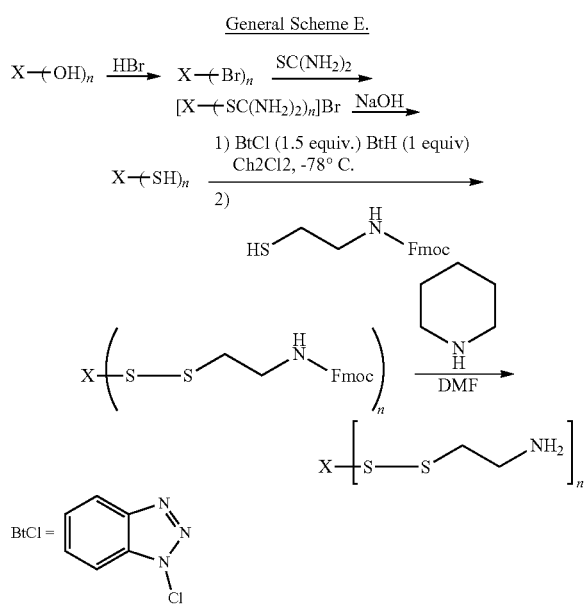

One skilled in the art will recognize that the above schemes can be used or modified based on synthetic methods known in the art of synthetic organic chemistry to synthesize prodrugs of the present disclosure. For example, more than one hydroxyl group of a precursor of $X(OR)_n$ may be substituted according to the above schemes. Similarity, modified cysteamine starting materials may be prepared and used to form prodrugs described herein, and the products of the above schemes may be further reacted to appropriately substitute the terminal —$NH_2$ group. In addition, well-known protecting groups may be used to improve selectivity. Non-limiting examples of suitable synthetic methodology may be found in U.S. Pat. No. 5,967,979, Frost et al., European Journal of Medicinal Chemistry (2016), 109, 206-215, Dasgupta, F. et al., Carbohydrate Research, (1980), 80, 346-349, Lu, K, et al., Tetrahedron (2004), 60(40), 8967-8973), and Carey, F. and Sundberg, R., *Advanced Organic Chemistry, Part B: Reactions and Synthesis*. Part B. $5^{th}$ Ed. New York: Springer, 2007, Khodari et al., Synthesis (2008), 1682-1684, Qian, W. and Pei, L Synlett (2006), 709-712, Wuts, P. and Greene, T., *Green's Protective Groups in Organic Synthesis*. $4^{th}$ Ed. New Jersey: John Wiley & Sons, 2007, Stellenboom, et al., Tetrahedron (2010), 66(17), 3228-3241, Stellenboom, et al., Tetrahedron Leters (2010), 51, 5309-5312, the entire contents of each of which are herein incorporated by reference in its entirety for all purposes. In particular, the general synthetic schemes set forth above can be applied to synthesize a prodrug using glycerol as a moiety as shown below in Schemes 1-4.

Scheme 1.

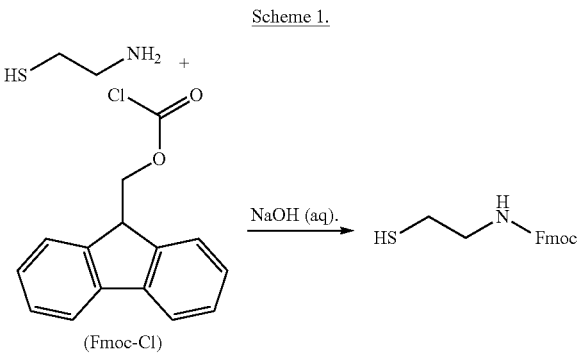

Scheme 2.

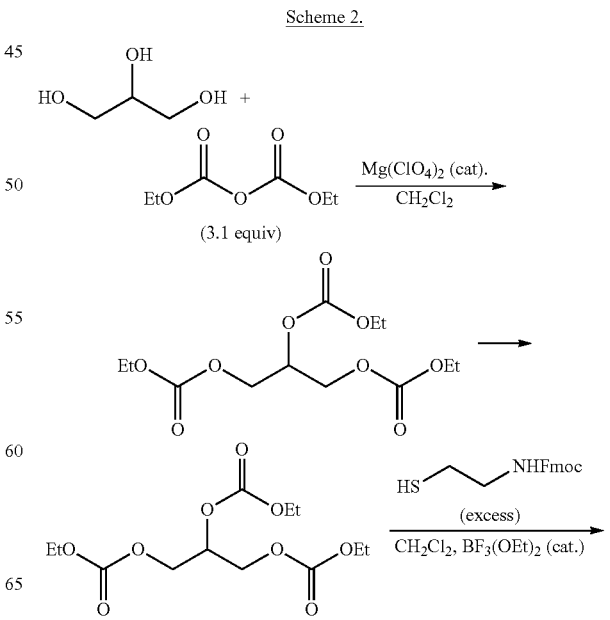

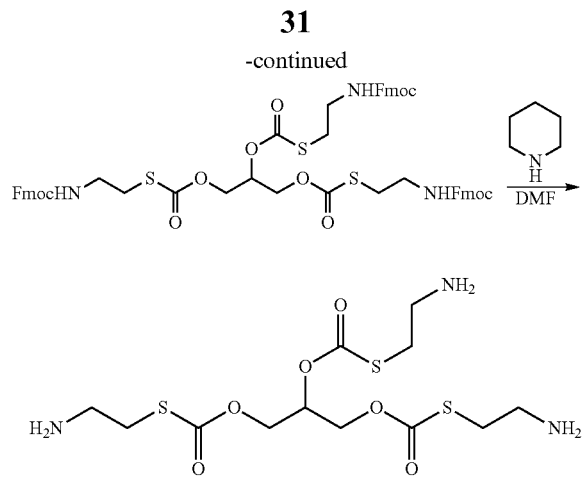

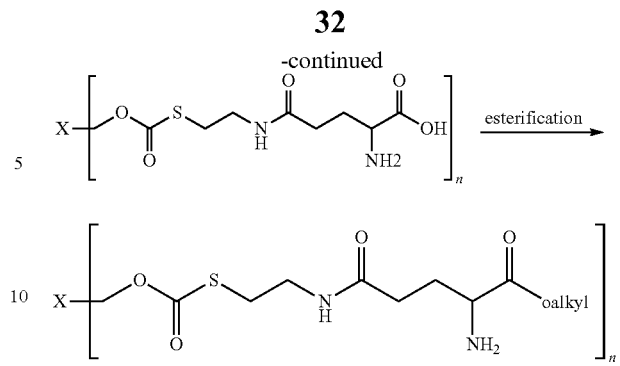

The general synthetic schemes described above can be applied to one or more of the hydroxyl groups on the precursors of X described herein or other hydroxylated, pharmaceutically acceptable moieties known to those skilled in the art.

EXAMPLES

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

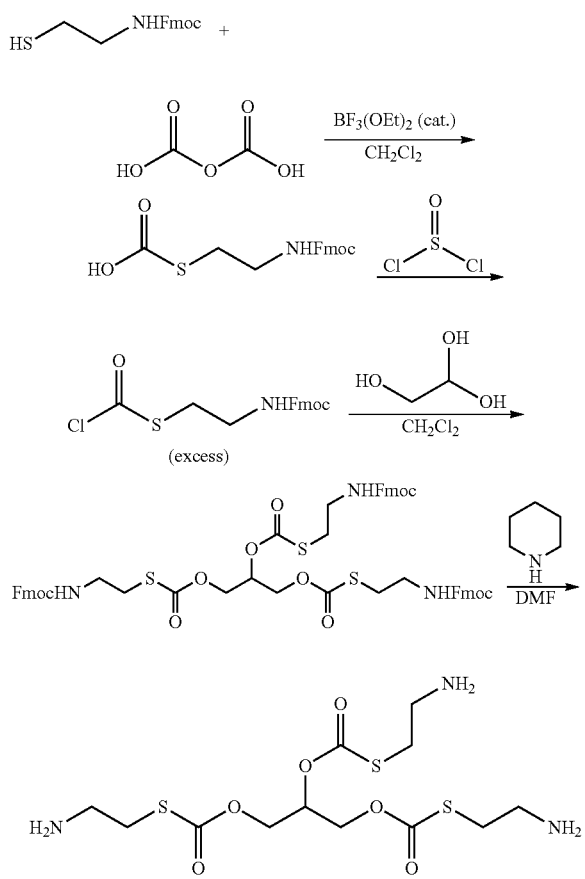

Scheme 3.

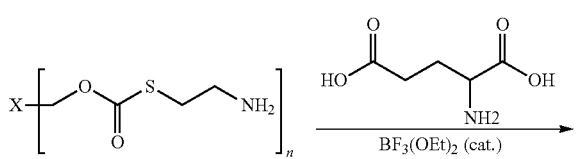

Scheme 4.

Example 1: Synthesis of Glycerol Cysteamine Acid Salts

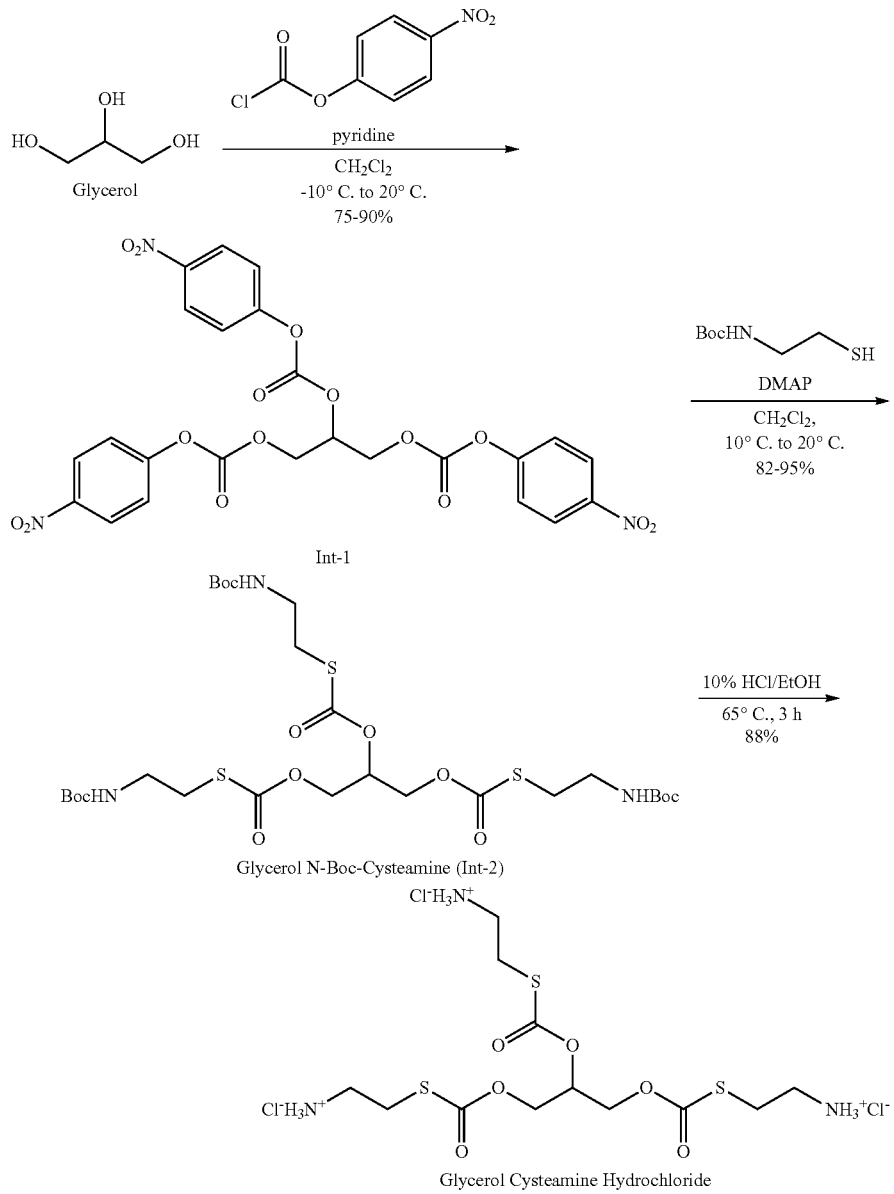

Synthesis of Intermediate 1 (Int-1)

Figure 1B:
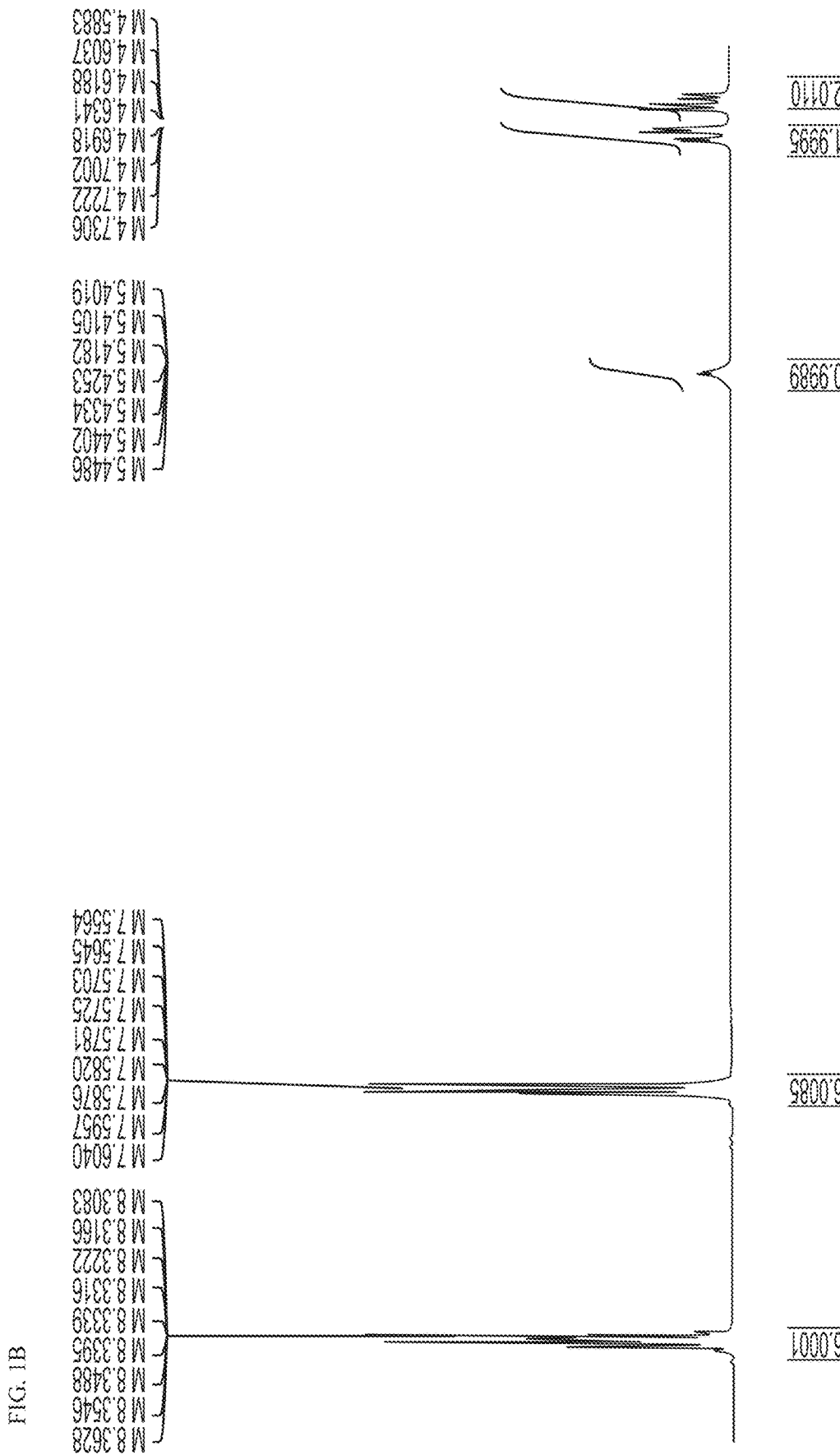
FIG. 1B is a $^1$H NMR spectrum confirming the structure of Int-1 formed as a product in Scheme 5.

4-Nitrophenyl chloroformate (3.0 eq.) was dissolved in dichloromethane and cooled to −10° C. Glycerol dissolved in pyridine (4.5 eq.) was then added ("reverse addition") via slow dropwise addition to the solution. The reaction mixture was warmed to 20° C. and stirred for 2 h. Upon completion, 1 N aq. HCl (5 eq.) was added to extract all the formed pyridine salt from the organics. The organic layer was then collected and further washed with 5% aq. NaHCO$_3$ and water (3×). After drying over Na$_2$SO$_4$, and filtering, the solvent was concentrated to yield the desired product (Scheme 5). Purification was accomplished via recrystallization from EtOAc/heptane, using EtOAc (2 volumes) to dissolve the solid, and heptane (1 volume) to facilitate slow crystallization overnight at 23° C. The precipitated product was collected and dried by vacuum filtration to yield purified Int-1 (FIG. 1A). The structure of Int-1 was confirmed by $^1$H NMR (FIG. 1B).

Synthesis of Glycerol N-Boc-Cysteamine (Int-2)

Figure 2:
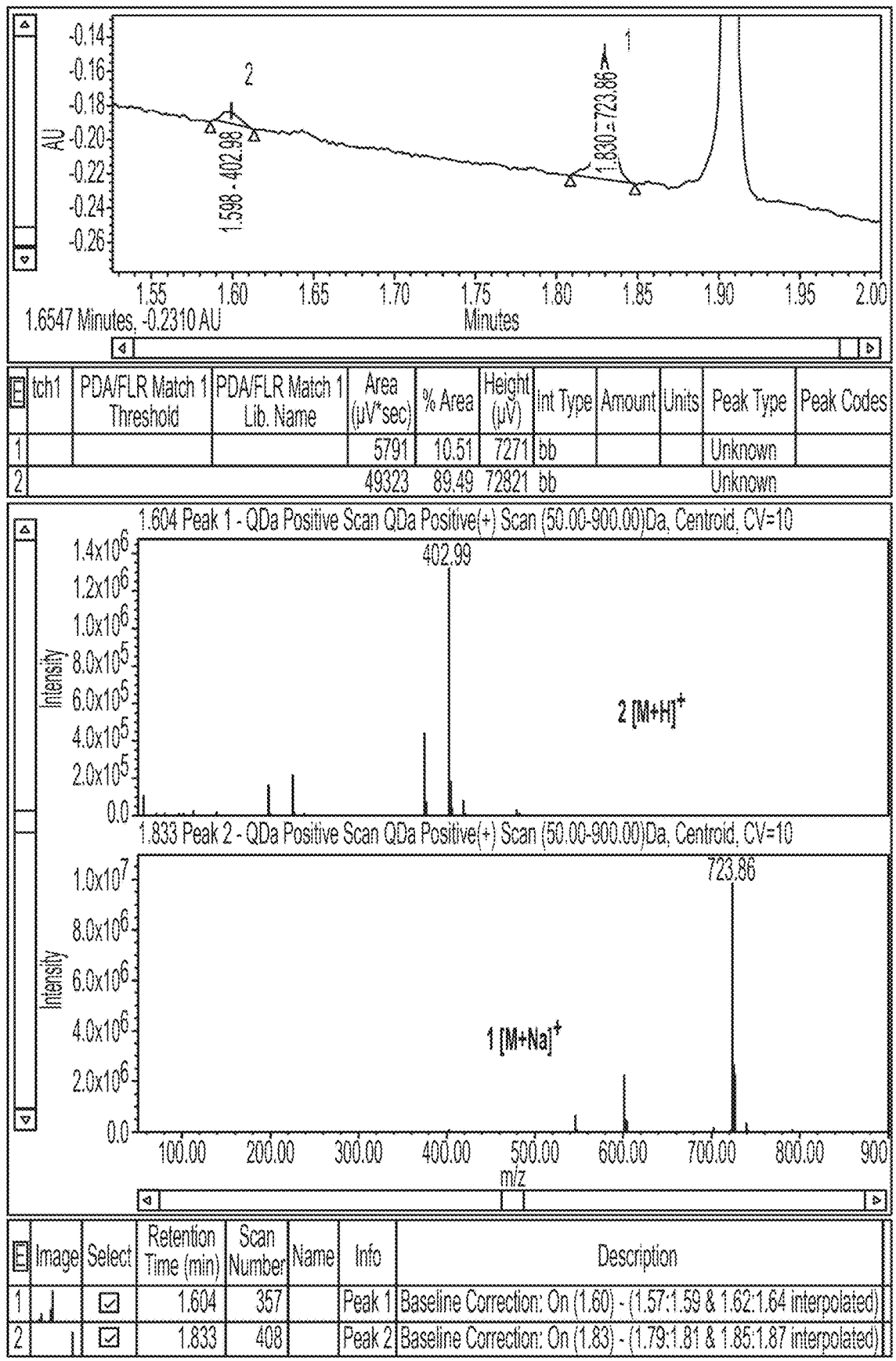
FIG. 2 shows UPLC/MS data confirming the formation of glycerol N-Boc-cysteamine (Int-2), as well as a minor dithiocarbonate byproduct also formed during the conversion shown in Scheme 5.
Figure 2:
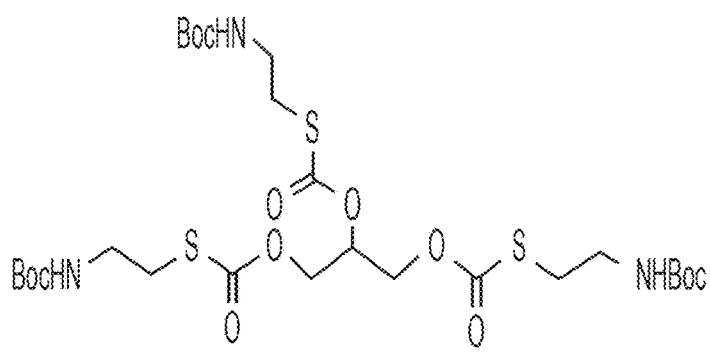
Figure 2:
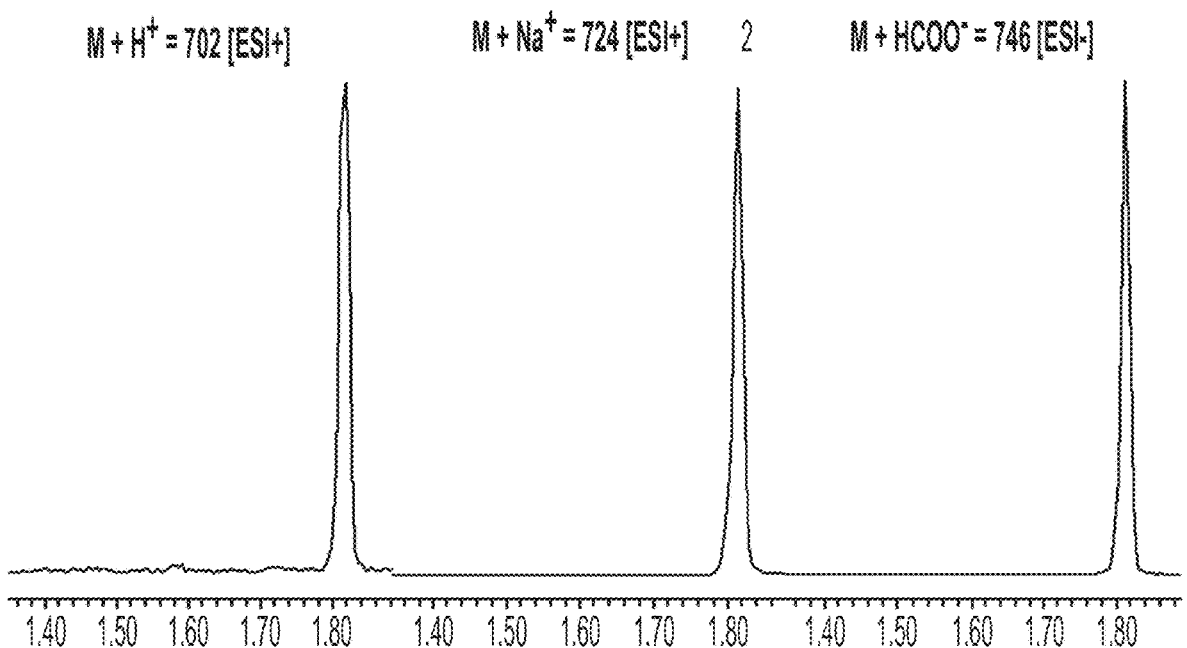
Figure 3:
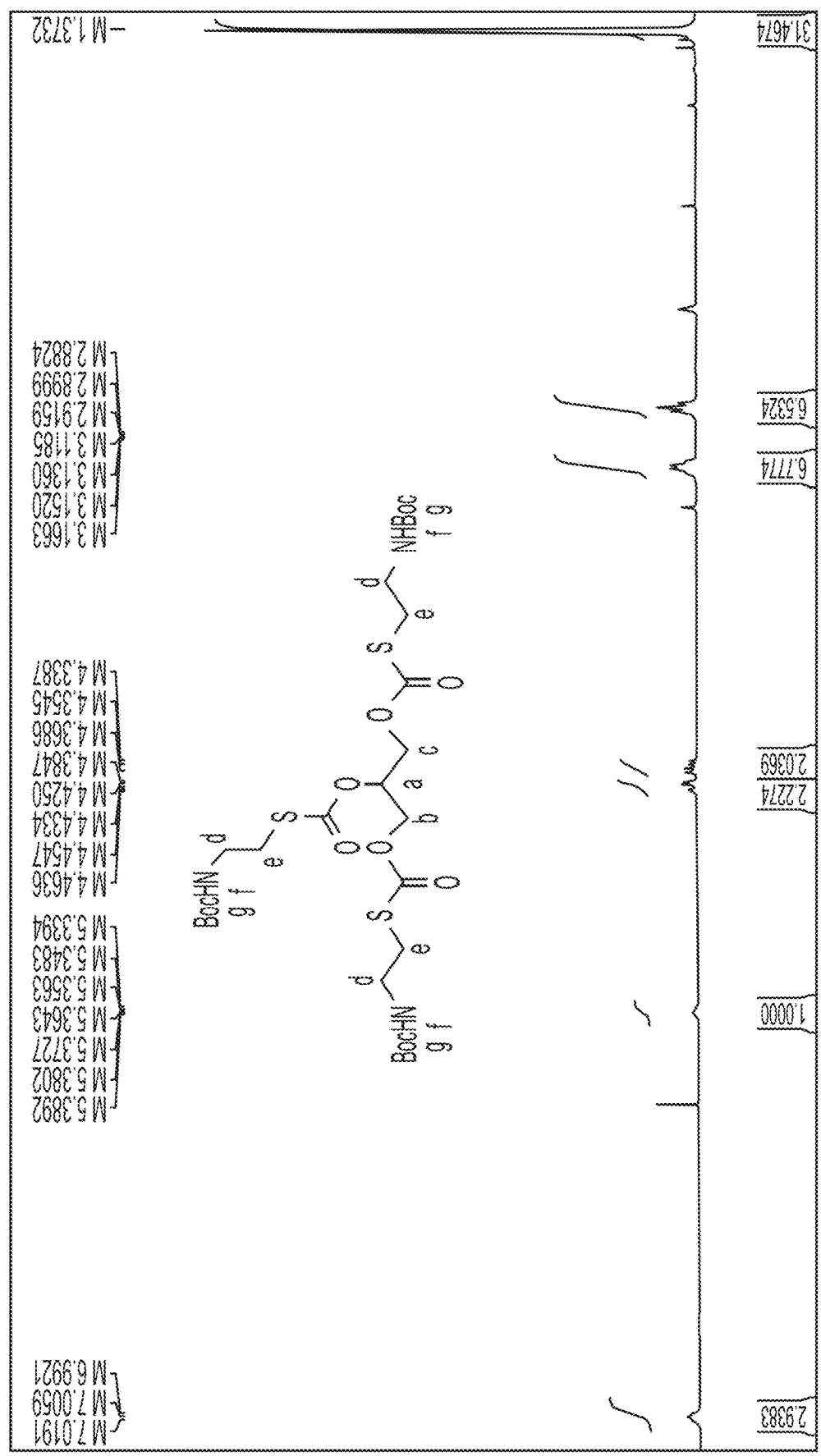
FIG. 3 shows a $^1$H NMR spectrum confirming the structure of glycerol N-Boc-cysteamine (Int-2) formed during the conversion shown in Scheme 5.
Figure 4:
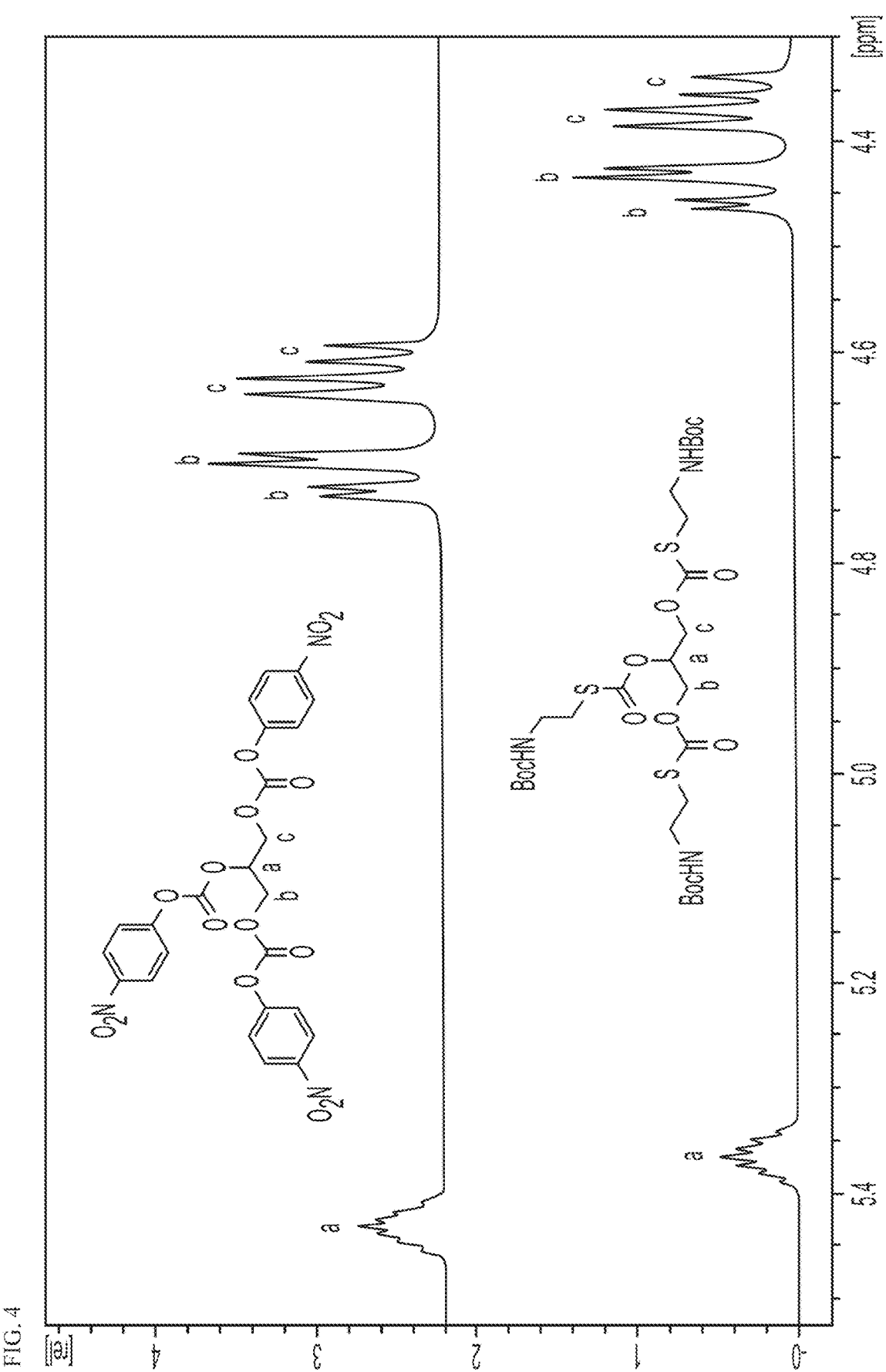
FIG. 4 shows a truncated set of $^1$H NMR spectra highlighting the key signals that differentiate Int-1 from glycerol N-Boc-cysteamine (Int-2).

Int-1 and N-Boc-cysteamine (3.0 eq.) were combined in dichloromethane at 20° C., followed by portionwise addition of DMAP (4.0 eq.). The reaction was stirred for 30 min at which time conversion was complete. The organics were washed (3×) with 1 N HCl to remove the DMAP salt, and further washed with K$_2$CO$_3$ (aq) to remove the 4-nitrophenol byproduct. Drying was accomplished with Na$_2$SO$_4$, followed by concentration of the solvent to afford the crude desired product. The structure of glycerol N-Boc-cysteamine was positively confirmed by UPLC/MS (FIG. 2) and $^1$H NMR (FIG. 3) and distinguished from Int-1 (FIG. 4).

Synthesis of Glycerol Cysteamine Hydrochloride

Figure 5:
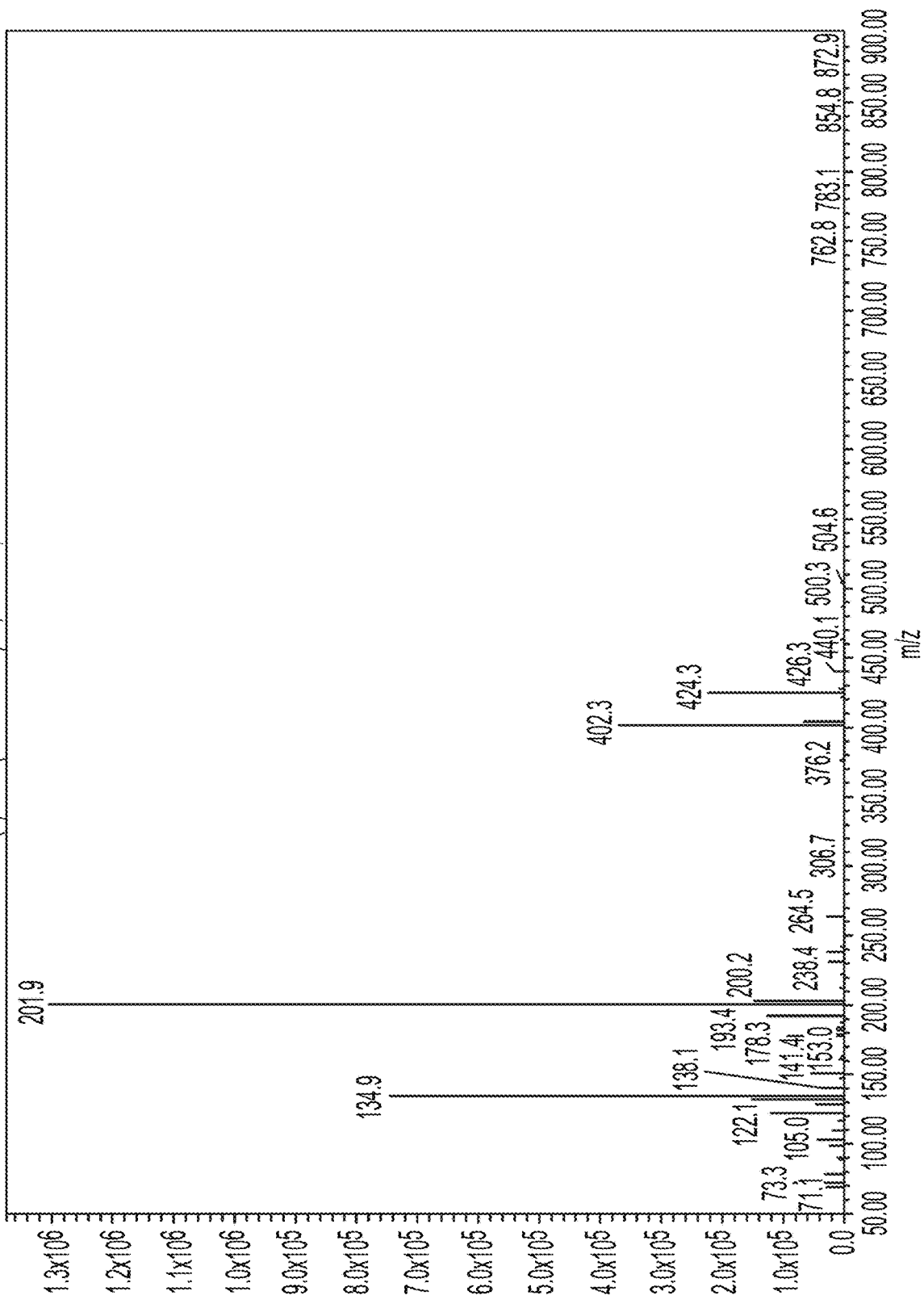
FIG. 5 shows UPLC/MS data confirming the formation of glycerol cysteamine hydrochloride from the corresponding glycerol N-Boc-cysteamine (Int-2), as shown in Scheme 5.
Figure 6:
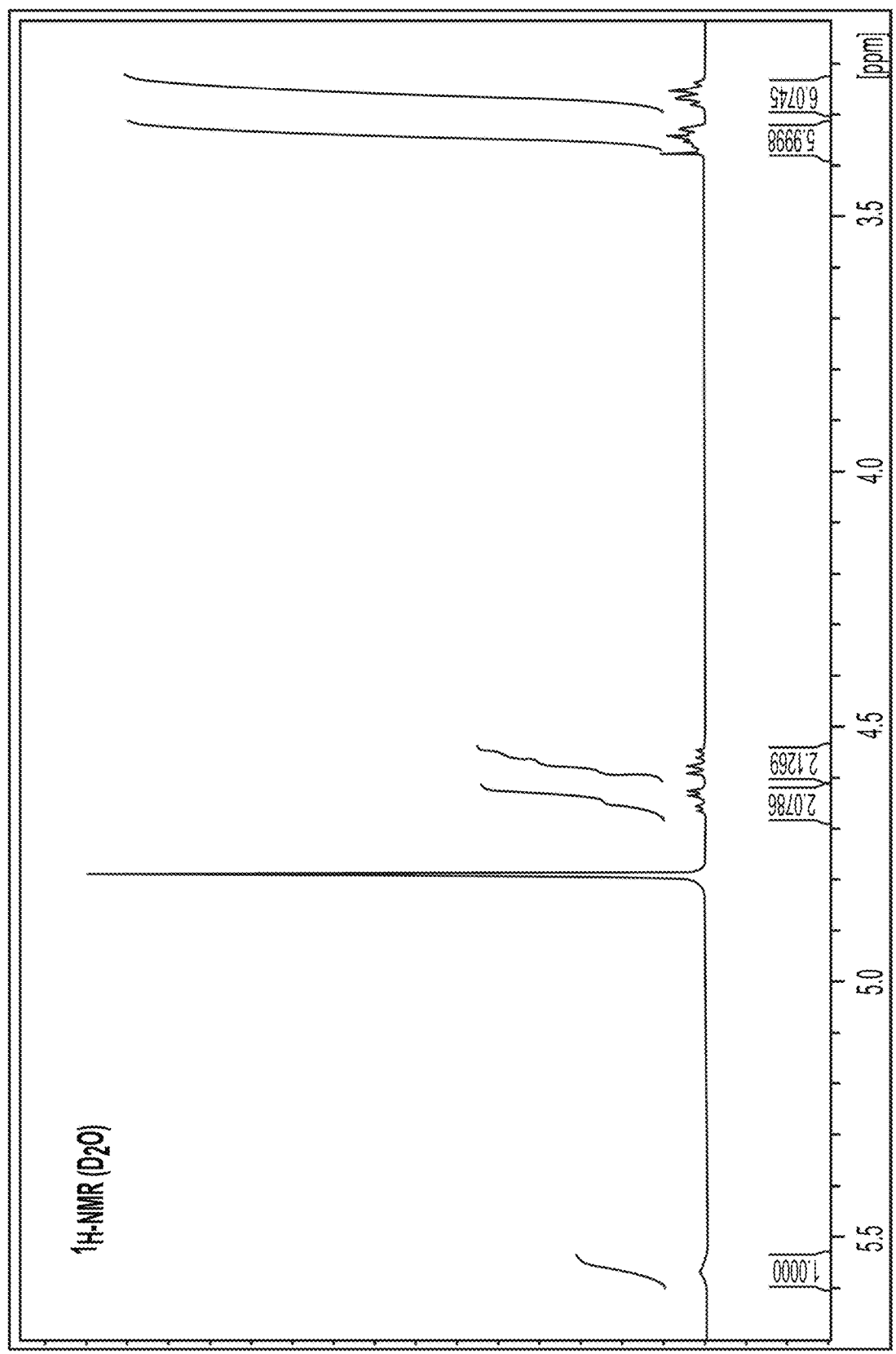
FIG. 6 shows a $^1$H NMR spectrum confirming the structure of glycerol cysteamine hydrochloride formed during the conversion shown in Scheme 5.

Glycerol N-Boc-Cysteamine was dissolved in a solution of 10% w/w HCl (gas) in EtOH (10 eq.) and the mixture was stirred at 65° C. over 3 h (Scheme 5). As the reaction progressed, a white solid precipitated out of the solution as a fine powder. Upon completion, the reaction mixture was cooled to 0° C. and stirred an additional 1 h. Solvent was partially removed under vacuum at which time MeOH was added. The contents were heated under vacuum at 40° C. for 1 h to remove the remainder of solvent, followed by drying in a desiccator under vacuum in the presence of a phosphoric anhydride (strong dehydrating agent). The structure of the obtained glassy solid was confirmed by UPLC/MS (FIG. 5) and $^1$H NMR (FIG. 6) to be the desired glycerol cysteamine hydrochloride salt.

Example 2: Synthesis of Reverse Glycerol Cysteamine Product (RP-1)

Synthesis of Glycerol Cysteamine Trifluoroacetate

Figure 7:
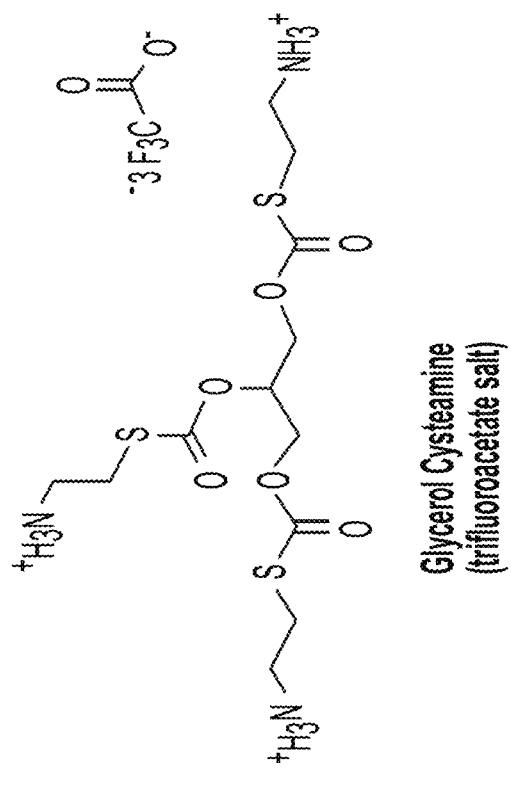
FIG. 7 shows UPLC/MS data confirming the formation of glycerol cysteamine trifluoroacetate from glycerol N-Boc-cysteamine (Int-2), as shown in Scheme 5.
Figure 7:
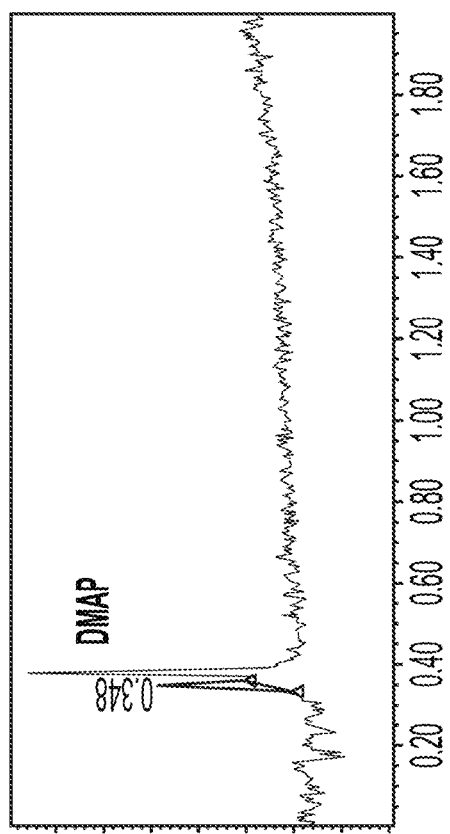
Figure 7:
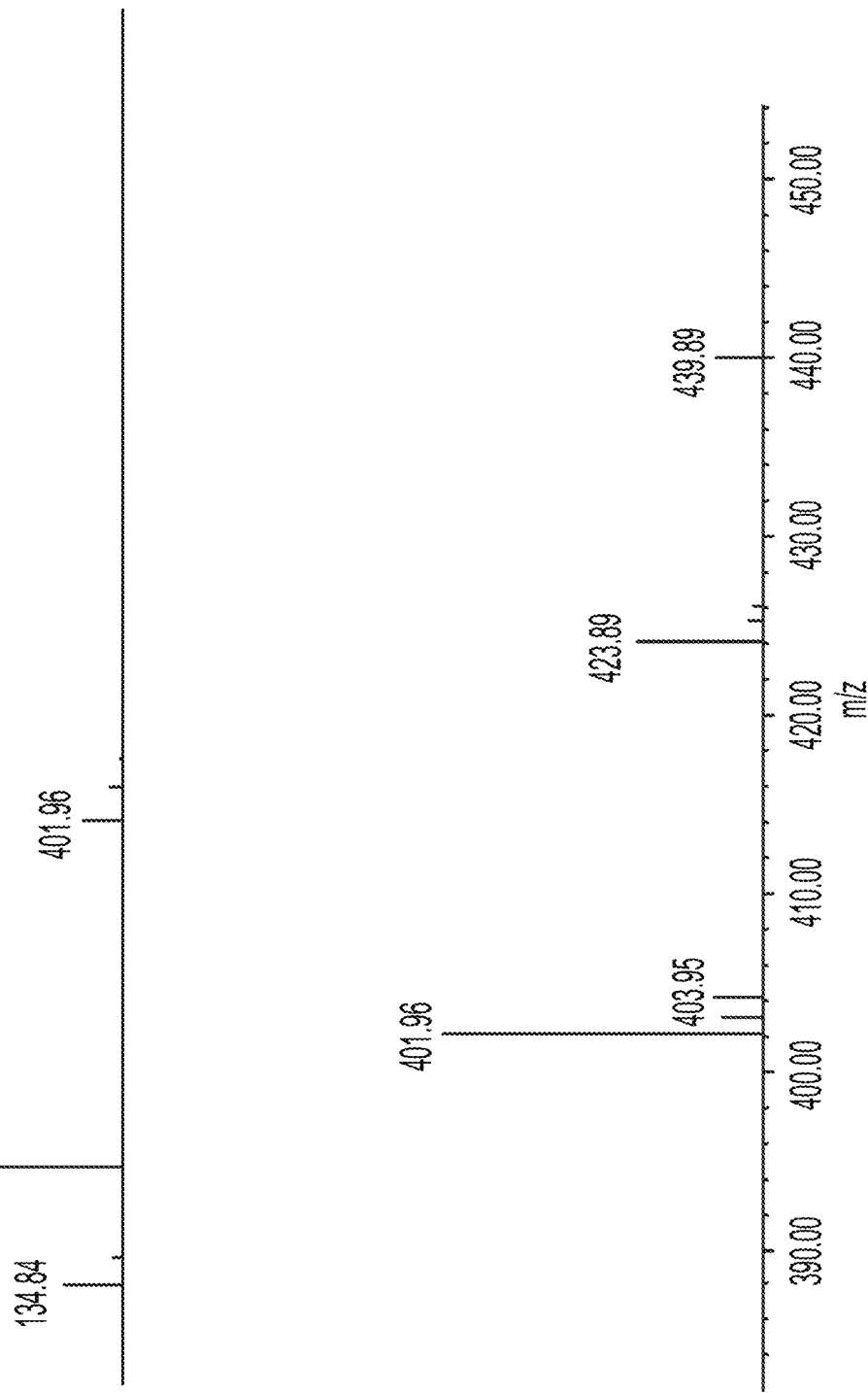

Glycerol N-Boc-Cysteamine was dissolved in dichloromethane. Trifluoroacetic acid (20 eq.) was added dropwise at 20° C. After 2 h, starting material was completely consumed and product formation was confirmed by UPLC/MS (FIG. 7). The glycerol cysteamine trifluoroacetate salt was extracted from the organic layer with water to provide an aqueous solution of the desired product (Scheme 6), used directly in the next step.

Figure 8:
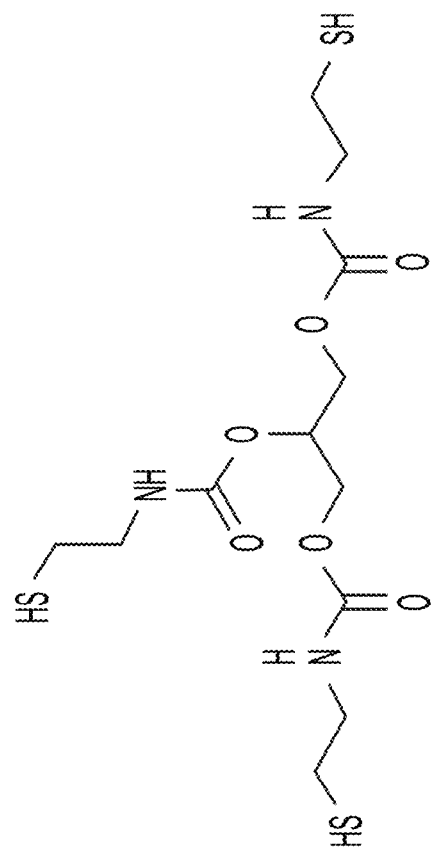
FIG. 8 provides UPLC/MS data confirming the formation of the reverse glycerol cysteamine free base, a rearrangement product in Scheme 6 formed by neutralization of glycerol cysteamine hydrochloride.
Figure 8:
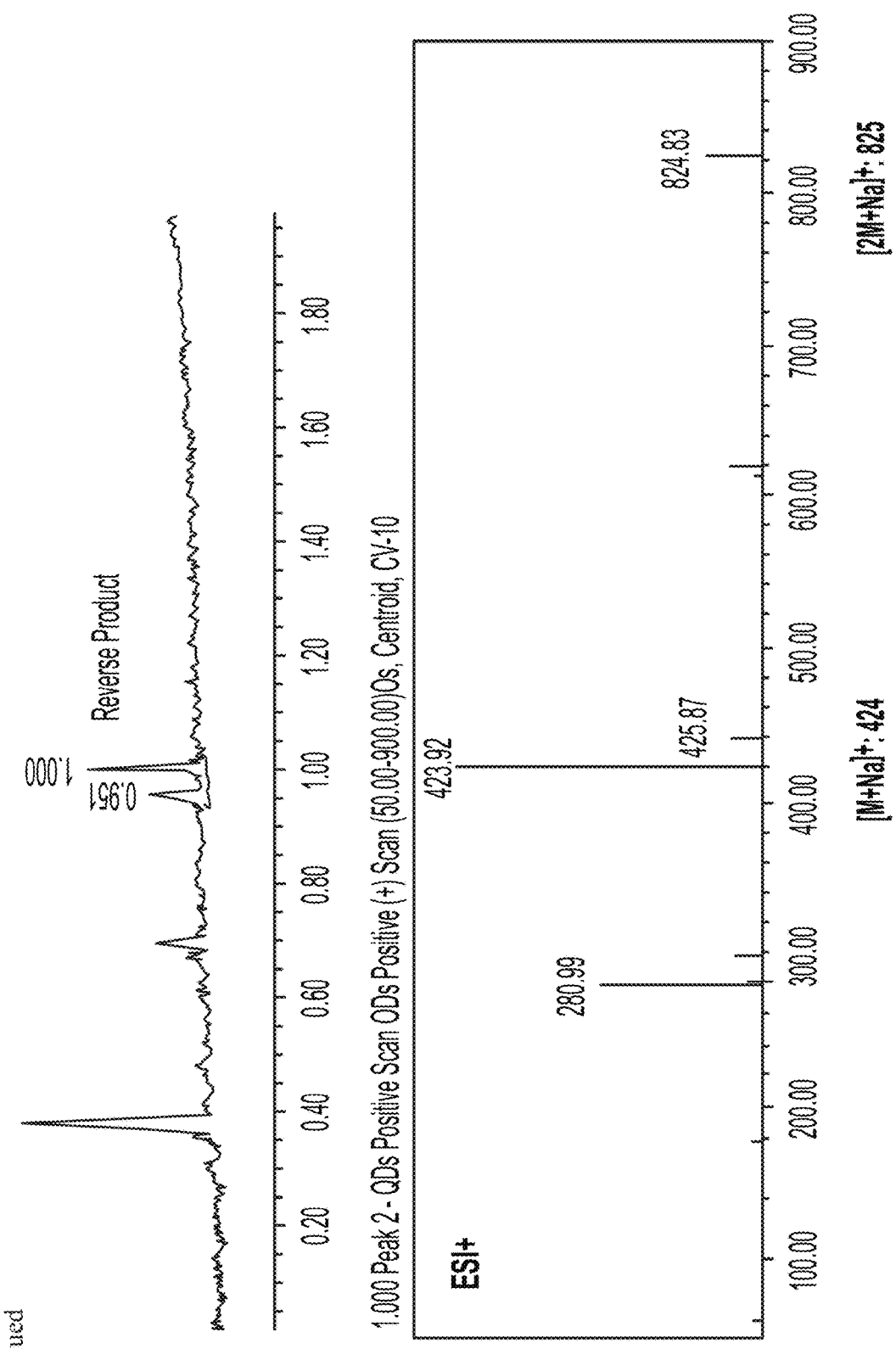
Figure 8:
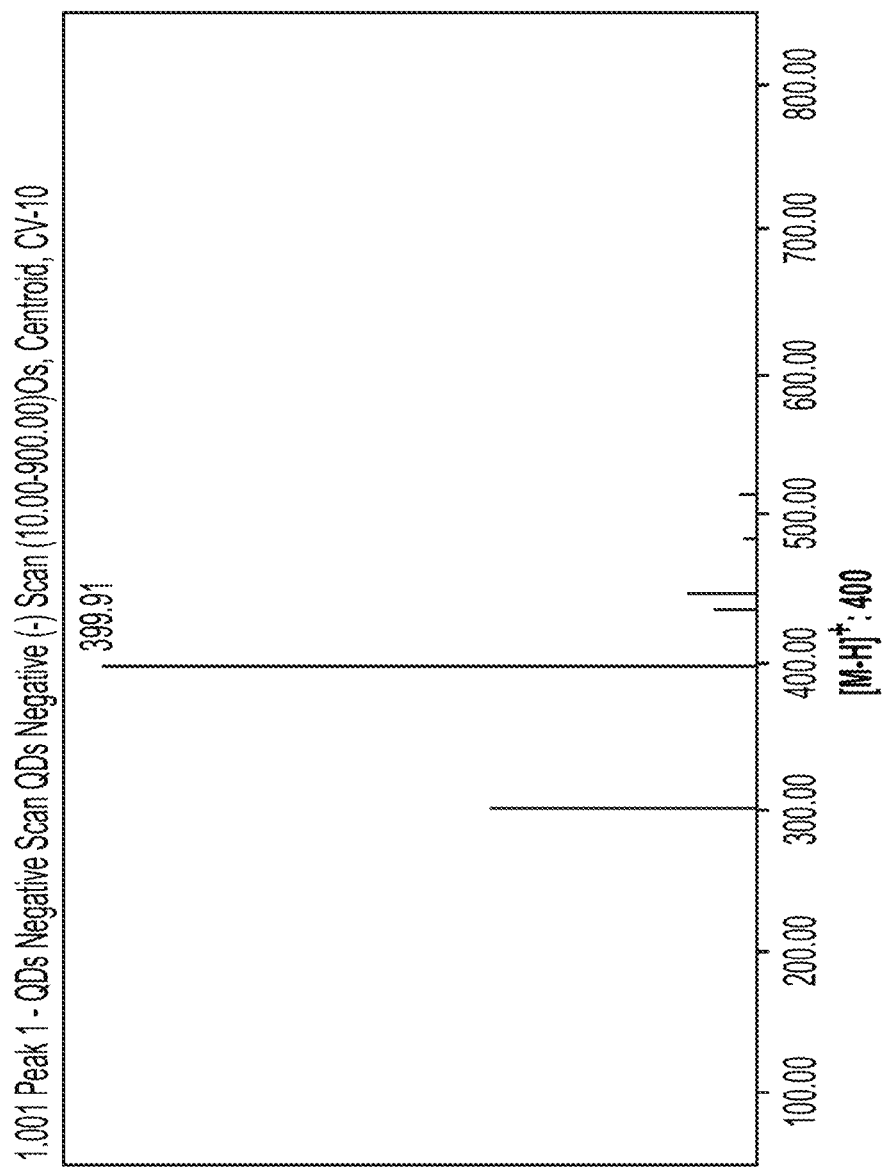
Figure 9:
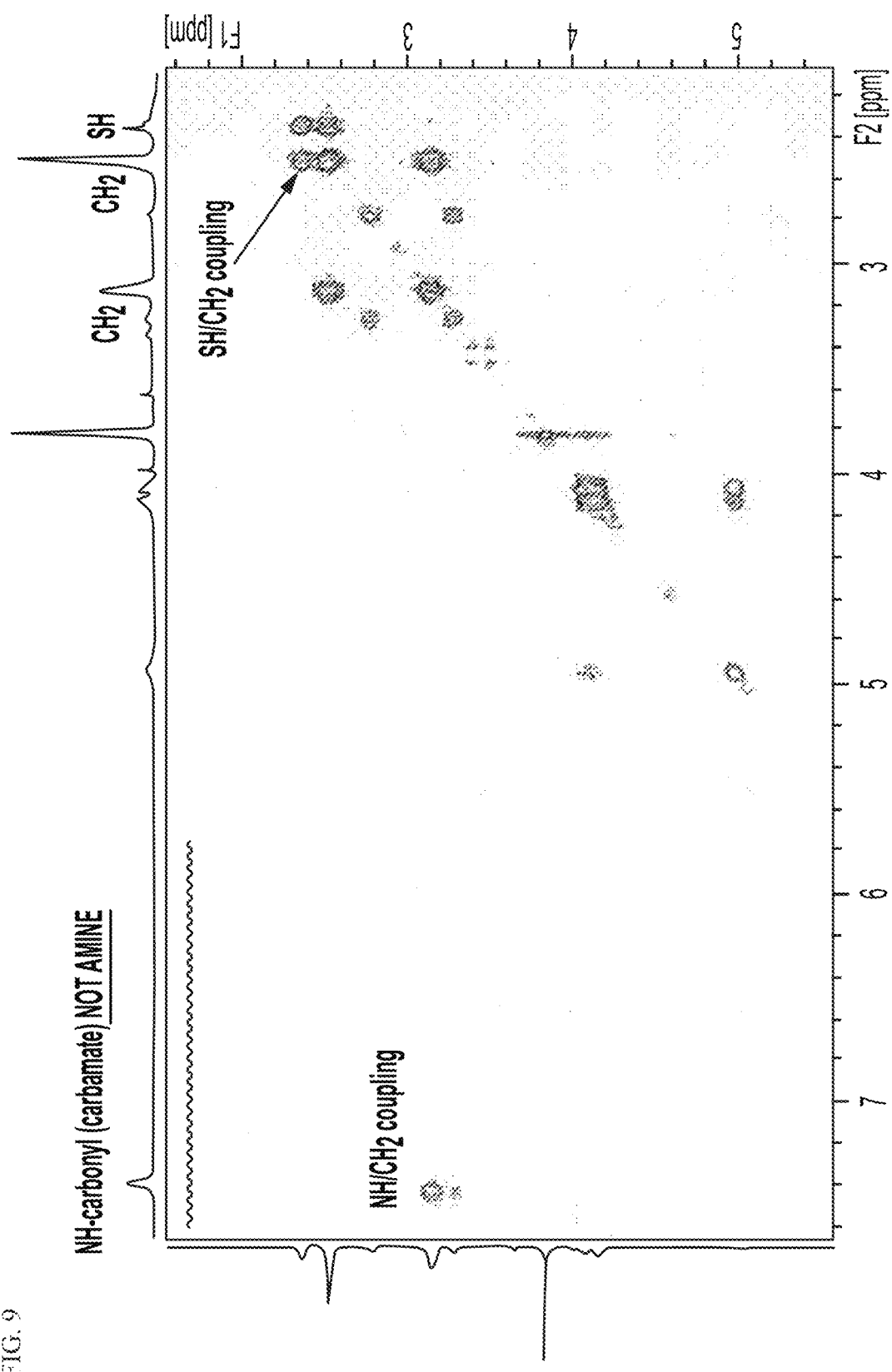
FIG. 9 provides a $^1$H-$^1$H COSY spectrum that is fully consistent with the carbamate structure shown as the reverse glycerol cysteamine free base product in Scheme 6.
Figure 10:
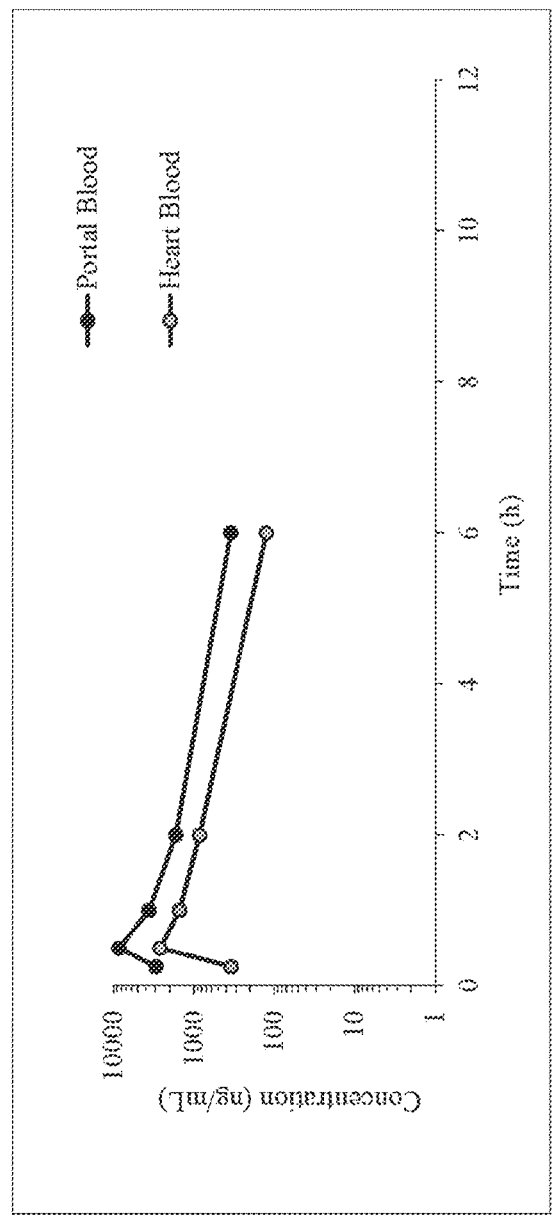
FIG. 10 is a plot of the area under the curve (AUC) showing the concentration of cysteamine hydrochloride (ng/ml) in portal blood and heart blood of rats over 6 h after oral (PO) dosing of glycerol cysteamine hydrochloride.
Figure 11:
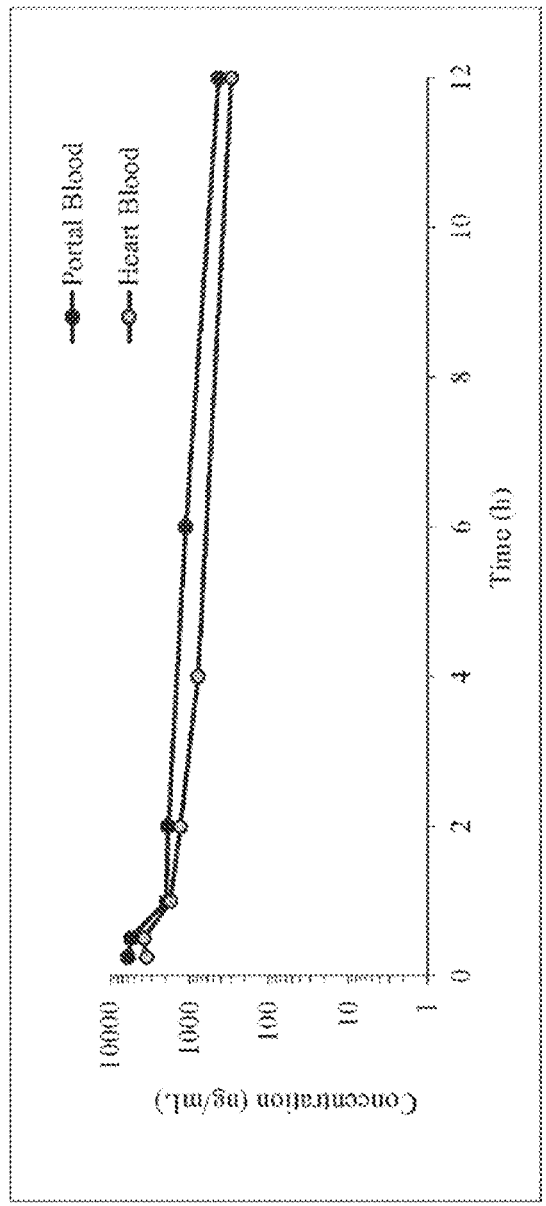
FIG. 11 is a plot of the area under the curve (AUC) showing the concentration of cysteamine hydrochloride (ng/ml) in portal blood and heart blood of rats over 12 h after oral (PO) dosing of cysteamine hydrochloride.

The aqueous solution of glycerol cysteamine trifluoroacetate prepared above was treated with 0.1 M NaOH dropwise until the solution was at pH 9-10 (Scheme 6). UPLC/MS indicated formation of the desired product based on a new peak with the same exact mass, but with a shift in retention time from the starting material (FIG. 8). After isolation, the structure of RP-1 was further verified by $^1$H-$^1$H COSY analysis (FIG. 9).

Example 3: Pharmacokinetic (PK) Study of Glycerol Cysteamine Hydrochloride

The objective of the PK study was to assess the pharmacokinetics of cysteamine in vivo, following oral dosing in rats of glycerol cysteamine hydrochloride (vehicle for PO administration: water, pH 4). Absorption and hepatic extrac-

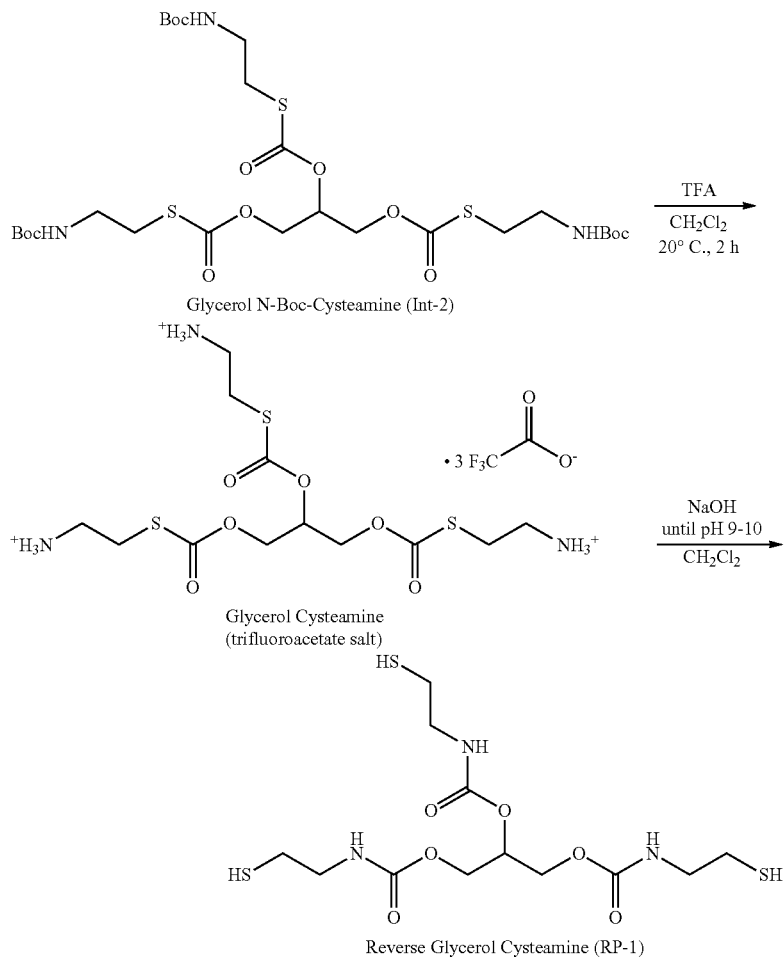

tion information after oral administration and blood sampling from portal vein and heart (HPV protocol) were evaluated.

Experimental design: 27 male CD rats (approximate body weight: 250-300 g) were each orally adminstered glycerol cysteamine hydrochloride ($MW_{salt}$=510.89; $MW_{freebase}$=401.07; purity=93.8%) at a target dose level of 100 mg/kg (dose volume=5 ml/kg). Blood samples were collected at intervals up to 24 h after dose administration (n=3 animals per each time point).

Sample Collection and Handling: After PO administration, blood samples were collected under deep Isofluorane anesthesia from portal vein and heart of each rat (3 rats per each time point). Blood was collected into potassium EDTA tubes at each of the following time points post-dose (actual times will be recorded): 0.25, 0.5, 1, 2, 4, 6, 8, 12 and 24 hours after dosing. All blood samples were thoroughly, but gently mixed following collection, placed on ice and centrifuged as soon as possible (2000 g for 5 min at 0° C.) to prepare plasma. Duplicate 50 μL aliquots of plasma samples were transferred in micronic tubes.

Plasma Sample Preparation:
1. Calibration standards (CS) and quality control (QC) plasma samples were prepared by adding 5 μL WS to 45 μL of fresh plasma into micronic tubes using Tecan.
2. Pseudo QC were prepared by adding 5 μL WSQC to 45 μL of water into micronic tubes using Tecan.
3. CS, QC, pseudo QC and blank were diluted with 200 μL of KCl solution (1.15%).
4. Plasma collection was performed by laboratory automation system (LAS). 50 μL whole plasma was transferred into micronic tubes containing 200 μL of KCl solution (1.15%).
5. All samples were added diluted? with 20 μL of glutathione ethyl ester as internal standard (0.01 mg/mL in water) and 100 μL of Ellman's reagent (10 mM in water).
6. The mixture was vortex-mixed for 1 min followed by the addition of 20 μL of 3% trichloroacetic acid.
7. The precipitated proteins were removed by centrifugation (3000 g×5 mins).
8. The samples were stored at −80° C. prior to analysis.
9. After thawing, sample supernatants were transferred to a 96 well plate using Hamilton and diluted with 0.1% HCOOH in water (1:5 dilution).

Plasma sample analysis: Samples were assayed for cysteamine using a method based on protein precipitation followed by HPLC/MS-MS analysis. Study samples were analyzed in discrete batches together with calibration standards (CS), used to construct calibration curves and blank samples (including also double blanks), used to assess specificity. Quality control samples (QC) were prepared to control the correct preparation of the calibration standards and to monitor the performance of the method. The results for cysteamine in plasma were subject to non-compartmental pharmacokinetic analysis using Phoenix WinNonlin v6.3 software for generation of appropriate pharmacokinetic parameters (e.g. Cmax, tmax, AUC0-24). The presence of prodrug and its products were monitored but not quantified in both portal and systemic plasma.

PK results: Taking into account the glycerol moiety, the correction factor between drug (cysteamine hydrochloride) and prodrug (glycerol cysteamine hydrochloride) was determined to be 1.5. Therefore, the corresponding cysteamine dose, administered as prodrug was 66.6 mg/kg. The data was normalized to 100 mg/kg cysteamine, applying the correction factor of 1.5. Cysteamine levels in portal plasma after prodrug administration were comparable to those observed after cysteamine hydrochloride administration. Systemic exposure was about 1.7 fold lower leading to different hepatic extraction. Cysteamine hepatic extraction was 0.3 when cysteamine hydrochloride was administered, while it was higher (EH=0.6) when the prodrug was administered. The fraction absorbed was comparable (Table 1). As the differences in hepatic extraction reflect the dose given, and not any difference in the nature of the drug, the conclusion based on this data is that the cysteamine hydrochloride is fully separated from the glycerol prodrug moiety in the gastrointestinal (GI) tract.

TABLE 1

PK Parameters from Rats Treated Orally with Test Compounds

| | Compound Administered | | | |
| --- | --- | --- | --- | --- |
| | Cysteamine Hydrochloride PO | | Glycerol Cysteamine Hydrochloride PO* | |
| Matrix | Plasma Heart | Plasma Portal | Plasma Heart | Plasma Portal |
| Cmax (ng/mL) | 3720 | 5400 | 2630 | 8520 |
| Tmax (h) | 0.50 | 0.50 | 0.50 | 0.50 |
| Clast (ng/mL) | 296 | 427 | 124 | 349 |
| Tlast (h) | 12.00 | 12.00 | 6.00 | 6.00 |
| AUClast (h * ng/mL) | 11200 | 16100 | 4580 | 11500 |
| AUCINF_obs (h * ng/mL) | 13200 | 19000 | 4830 | 12300 |
| AUC_% Extrap_obs (%) | 15.0 | 15.2 | 5.17 | 6.35 |
| HL_Lambda_z (h) | 4.64 | 4.68 | 1.40 | 1.55 |
| MRTINF_obs (h) | 6.05 | 6.03 | 1.94 | 1.91 |
| SE_Cmax (ng/mL) | 770 | 1890 | 458 | 315 |
| SE_AUClast (h * ng/mL) | 955 | 1680 | 546 | 866 |
| AUC0-6 h (h * ng/mL) | 7980 | 11500 | 4580 | 11500 |
| Fa % | 16.1 | | 22.8 | |
| EH | 0.304 | | 0.602 | |

The invention claimed is:
1. A compound according to formula (I),

$$X(\text{—R})_n \quad \text{(I)}$$

or a pharmaceutically acceptable salt, solvate, or ester thereof,
wherein:
X is a pharmaceutically acceptable moiety;
R comprises a moiety which releases cysteamine after administration to a subject;
$X(R)_n$ is: (a) derived from a carbohydrate, a sugar alcohol, or polymeric alcohol, wherein at least one —OH group of the carbohydrate, the sugar alcohol, or the polymeric alcohol is replaced by R; or (b) derived from glycerol, wherein at least one —OH group of glycerol is replaced by R; and n is a number from 1 to 100.

2. The compound of claim 1, wherein X(R)$_n$ is derived from a carbohydrate, a sugar alcohol, or polymeric alcohol, wherein at least one —OH group of the carbohydrate, the sugar alcohol, or the polymeric alcohol is replaced by R.

3. The compound of claim 1, wherein X(R)$_n$ is derived from polymeric alcohol, wherein at least one —OH group of the polymeric alcohol is replaced by R.

4. The compound of claim 1, wherein X(R)$_n$ is derived from glycerol, wherein at least one —OH group of glycerol is replaced by R.

5. The compound of claim 2, wherein the carbohydrate is selected from the group consisting of a monosaccharide, a disaccharide, an oligosaccharide, a polysaccharide, cellulose, a modified cellulosic, and starch.

6. The compound of claim 1, wherein R comprises cysteamine, or a substituted form thereof, which is linked to X through a linking group which can be cleaved in vivo, thereby releasing cysteamine, or the substituted form thereof.

7. The compound of claim 6, wherein the substituted form of cysteamine has the following structure:

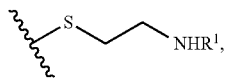

wherein R$^1$ is

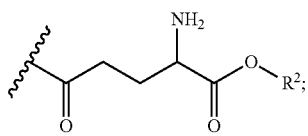

and each R$^2$ is independently H or an alkyl.

8. The compound of claim 6, wherein the substituted form of cysteamine has the following structure:

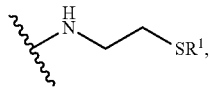

wherein R$^1$ is

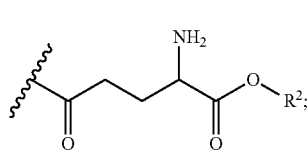

and each R$^2$ is independently H or an alkyl.

9. The compound of claim 6, wherein the linking group forms a thiocarbonate or thioester which is hydrolyzed enzymatically in vivo, thereby releasing cysteamine, or the substituted form thereof.

10. The compound of claim 1, having a structure according to formula (IIA), (IIB), or (IIE)

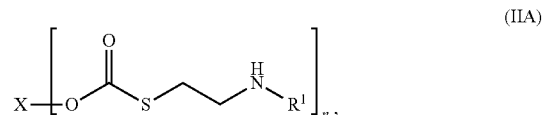

(IIA)

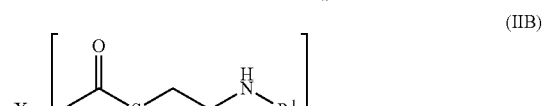

(IIB)

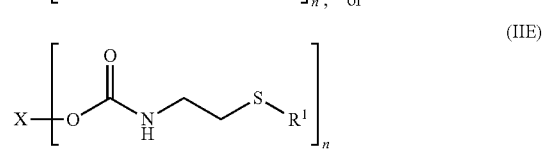

(IIE)

or a pharmaceutically acceptable salt, solvate, or ester thereof, wherein:

each R$^1$ is independently H or

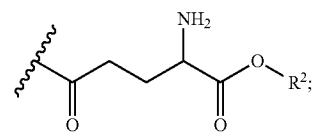

and each R$^2$ is independently H or an alkyl.

11. The compound of claim 1, having a structure according to formula (IIA)

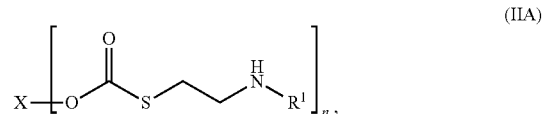

(IIA)

or a pharmaceutically acceptable salt, solvate, or ester thereof, wherein:

each R$^1$ is independently H or

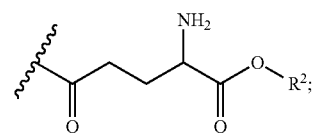

and each R$^2$ is independently H or an alkyl.

12. The compound of claim 6, wherein the linking group forms a sulfoxide which is reduced and cleaved enzymatically in vivo, thereby releasing cysteamine or the substituted form thereof.

13. The compound of claim 12, having a structure according to formula (IIC)

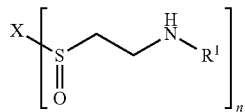
(IIC)

or a pharmaceutically acceptable salt, solvate, or ester thereof,
wherein:
each R¹ is independently H or

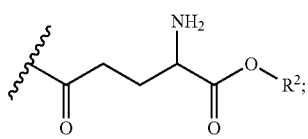

and
each R² is independently H or an alkyl.

14. The compound of claim 6, wherein the linking group forms a disulfide bond which is reduced in vivo, thereby releasing cysteamine.

15. The compound of claim 14, having a structure according to formula (IID)

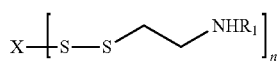
(IIID)

or a pharmaceutically acceptable salt, solvate, or ester thereof,
wherein:
each R¹ is independently H or

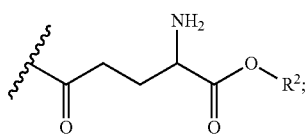

and
each R² is independently H or an alkyl.

16. The compound of claim 1, having a structure according to formula (III)

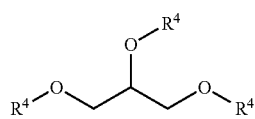
(III)

wherein:
each R⁴ is independently H,

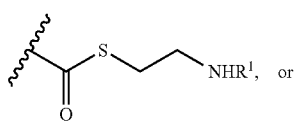

-continued

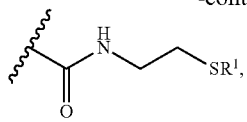

and at least one R is

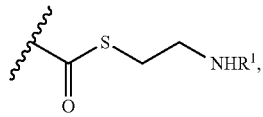

each R¹ is independently H or

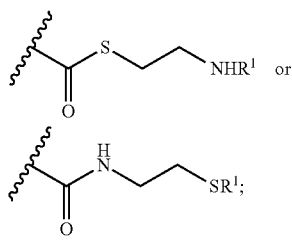

and each R² is independently H or alkyl.

17. The compound of claim 16, wherein each R⁴ is

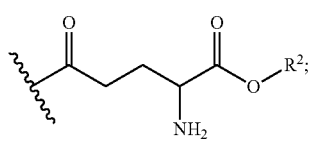

each R¹ is independently H or

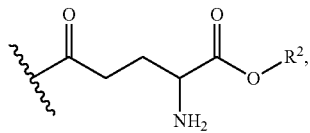

and each R² is independently H or alkyl.

18. The compound of claim 11, having the following structure:

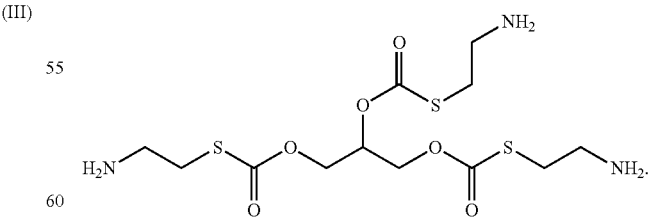

19. A pharmaceutical composition comprising a compound of claim 1.

20. The pharmaceutical composition according to claim 19, further comprising a corticosteroid.

* * * * *

UNITED STATES PATENT AND TRADEMARK OFFICE
CERTIFICATE OF CORRECTION

| | | |
|---|---|---|
| PATENT NO. | : 11,357,750 B2 | Page 1 of 1 |
| APPLICATION NO. | : 16/480773 | |
| DATED | : June 14, 2022 | |
| INVENTOR(S) | : Perrett et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 83 days.

Signed and Sealed this
Twenty-ninth Day of August, 2023

*Katherine Kelly Vidal*

Katherine Kelly Vidal
*Director of the United States Patent and Trademark Office*